United States Patent [19]

Bodor

[11] Patent Number: 5,017,618

[45] Date of Patent: May 21, 1991

[54] LABILE DERIVATIVES OF KETONE ANALOGS OF 3-SUBSTITUTED-1-ALKYLAMINO-2-PROPANOLS AND THEIR USE AS BETA-ADRENERGIC BLOCKERS

[75] Inventor: Nicholas S. Bodor, Gainesville, Fla.

[73] Assignee: University of Florida, Gainesville, Fla.

[21] Appl. No.: 408,778

[22] Filed: Sep. 18, 1989

Related U.S. Application Data

[63] Continuation-in-part of Ser. No. 338,205, Apr. 14, 1989, abandoned, which is a continuation of Ser. No. 26,002, Mar. 16, 1987, abandoned.

[51] Int. Cl.$^5$ .................... A61K 31/15; C07C 251/38
[52] U.S. Cl. .................... 514/640; 514/236.2; 514/312; 514/415; 514/439; 514/467; 514/469; 514/470; 514/524; 514/546; 514/597; 514/620; 514/625; 514/630; 514/639; 514/651; 544/134; 546/158; 549/466; 549/468; 549/450; 549/451; 549/30; 548/182; 548/146; 548/200; 548/201; 548/503; 558/422; 560/142; 564/51; 564/165; 564/220; 564/251; 564/256; 564/257; 564/258; 564/265; 564/344

[58] Field of Search .................... 544/134; 546/158; 549/30, 450, 451, 466, 468; 548/146, 200, 201, 182, 503; 558/422; 560/142; 564/257, 165, 220, 251, 256, 258, 265, 51; 514/236.2, 312, 415, 439, 467, 469, 470, 524, 546, 597, 620, 625, 630, 639, 640, 651

[56] References Cited

U.S. PATENT DOCUMENTS 4,521,414 6/1985 Chiou et al. .................... 514/229

FOREIGN PATENT DOCUMENTS 2070067 9/1971 France.
88/1226 10/1988 South Africa.
1253710 11/1971 United Kingdom.

OTHER PUBLICATIONS

Bodor et al, *J. Med. Chem.*, vol. 31, No. 1, 1988, 100–106.
Ahmed et al, *J. Pharm. Belg.* 37(3), 214–217 (1982), abstracted in *Chem. Abstracts*, vol. 97, 188158n (1982).
Gnit'ko et al, *Zh. Evol Biokhim Fiziol.*, 1972, 8(2), 194–201, abstracted in *Chem. Abstracts*, vol. 77, 70809j (1972).

*Primary Examiner*—Bernard I. Dentz
*Attorney, Agent, or Firm*—Mary Katherine Baumeister; Dennis P. Clarke

[57] ABSTRACT

Compounds having the formula

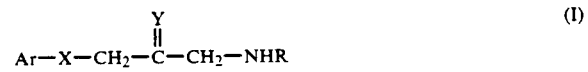

and their pharmaceutically acceptable acid addition salts, wherein —X— is —O—, —CH$_2$— or —; =Y is =O or a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties; are useful as β-adrenergic blocking agents and are of particular interest in the treatment of glaucoma or for lowering intraocular pressure.

86 Claims, 2 Drawing Sheets

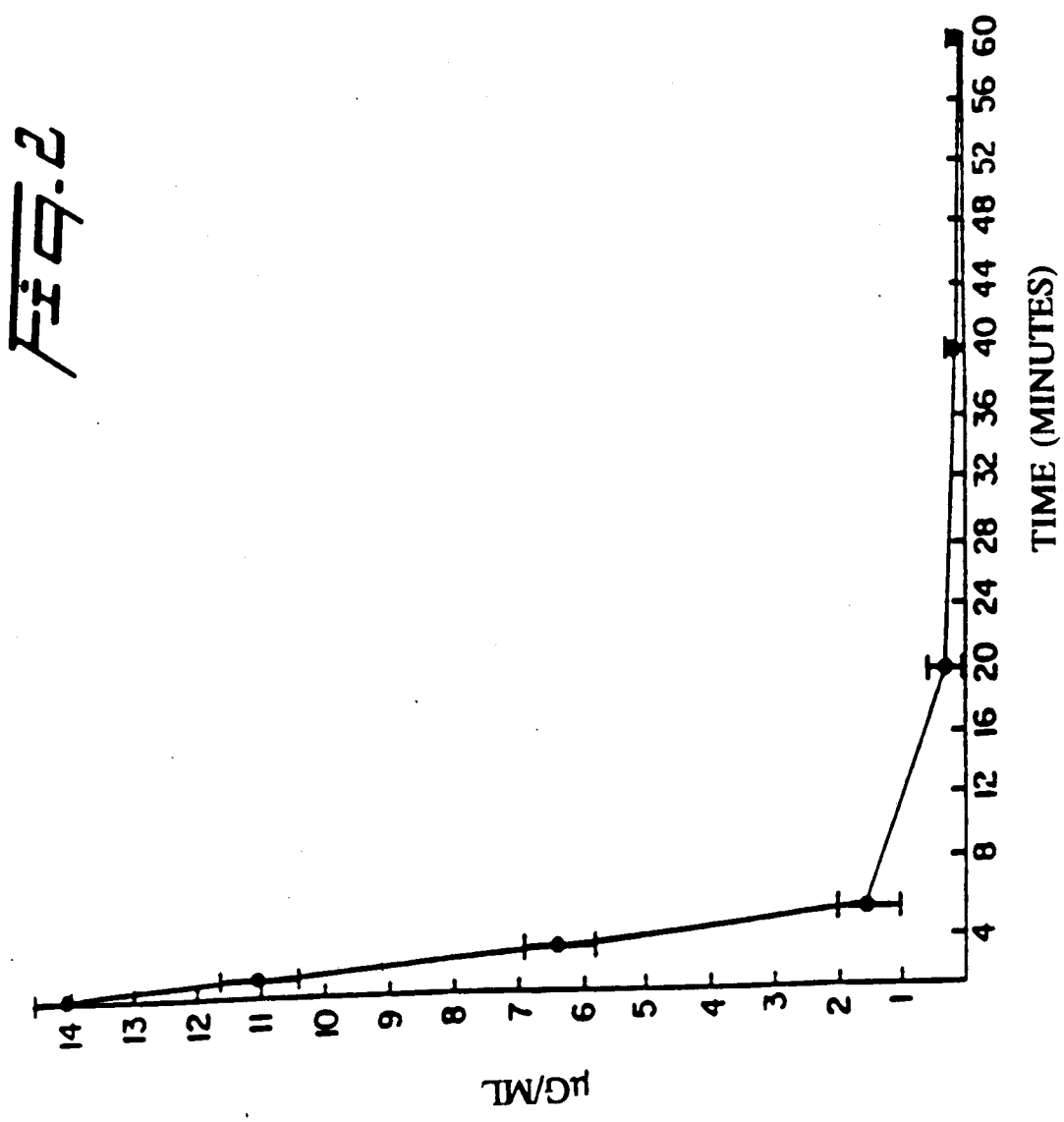

5,017,618

LABILE DERIVATIVES OF KETONE ANALOGS OF 3-SUBSTITUTED-1-ALKYLAMINO-2-PROPANOLS AND THEIR USE AS BETA-ADRENERGIC BLOCKERS

The research leading to the present invention was supported by NIH Grant RO1 EY05800. The United States Government has certain rights in the present invention.

CROSS-REFERENCE TO RELATED APPLICATIONS

This application is a continuation-in-part of applicant's copending application Ser. No. 07/338,205, filed Apr. 14, 1989, now abandoned, which is a continuation of applicant's Ser. No. 07/026,002, filed Mar. 16, 1987, now abandoned, incorporated by reference herein in their entirety and relied upon.

FIELD OF THE INVENTION

The present invention relates to novel 3-substituted-1-alkylamino-2-propanol derivatives having $\beta$-adrenergic blocking properties, to pharmaceutical compositions containing same and methods of treatment involving their use.

BACKGROUND OF THE INVENTION $\beta$-Adrenergic blockers were first reported to be useful for the therapeutic treatment of glaucoma in 1967 [Phillips et al, *Brit. J. Ophthal.*, 1967, 51, 222]. In 1978 timolol was approved for market use and since that time the drug has become very popular with ophthalmologists as an effective antiglaucoma agent. Recently, however, a vast number of serious cardiovascular, respiratory, CNS and ocular side effects secondary to topical ocular timolol administration has been reported [Ahmad, *The Lancet*, 1979, 2, 1028; Buskirk, *Ophthalmology*, 1980, 87, 447; Mishra et al, *J. Anaesth.*, 1983, 55, 897; and Linkewich et al, *Am. J. Hosp. Pharm.*, 1981, 38, 699]. Currently, timolol is no longer the sole $\beta$-blocker used to treat glaucoma. Befanolol, carteolol and metipranolol were introduced recently and a number of other newer $\beta$-adrenergic antagonists (e.g., L-bunolol, betaxolol, celiprolol, cetamolol etc.) are currently under investigation as antiglaucoma agents.

It became desirable to design an antiglaucoma drug which could be delivered to the eye compartments in a sustained and controlled manner with minimal systemic absorption and/or no systemic side effects.

It was previously found that after topical application to the eye, esters of adrenalone but not adrenalone itself can be converted via a reduction-hydrolysis sequence to deliver adrenaline (epinephrine) at the iris-ciliary body, the desired site of action [Bodor et al, *Exp. Eye. Res.*, 1984, 38, 621]. Research was conducted to ascertain whether lipophilic ketones could also be reduced in the iris-ciliary body.

It was hypothesized that ketone precursors of $\beta$-blockers which are also $\beta$-hydroxylamines like adrenaline could then possibly be converted to the active $\beta$-blockers in the iris-ciliary body by a reductive process. Various attempts, however, to synthesize the ketones corresponding to a number of $\beta$-blockers (i.e., propranolol, timolol, carteolol etc.) failed, due to the chemical instability of these $\beta$-amino-ketone ethers.

A few ketones corresponding to $\beta$-blockers or analogs thereof have been previously described in the art. Thus, Ahmed et al, *J. Pharm. Belg.* 37(3), 214–217 (1982), abstracted in *Chem. Abst.*, Vol. 97, 188158n (1982), have described reacting N-chlorosuccinimide and N-bromosuccinimide with propranolol hydrochloride in an attempt to develop a titrimetic method for detection of propranolol. Obtained as a reaction product of propranolol hydrochloride with N-chlorosuccinimide were succinimide and a dichlorinated ketone of the formula

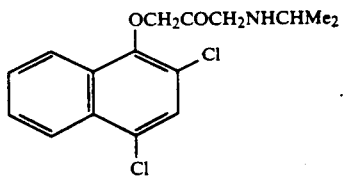

Further, French Patent Publication No. 2070067 published Sept. 10, 1971 has described, as intermediates to $\beta$-blockers, ketones of the formula

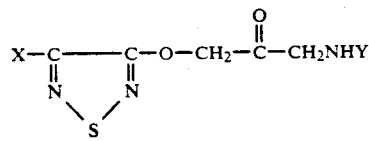

wherein Y is a lower alkyl or lower hydroxyalkyl radical and X is chloro, lower alkyl, lower alkoxy, phenyl, benzyl, morpholino, piperidyl, hydroxypiperidyl or N-(lower alkyl)-piperazinyl. The patent teaches reduction by chemical means or by fermentation of the ketones to the desired final products. Specific ketones named in the French document are 3-morpholino-4-(3-tert-butylamino-2-oxopropoxy)-1,2,5-thiadiazole, 3-chloro-4-(3-tert-butylamino-2-oxopropoxy)-1,2,5-thiadiazole, 3-chloro-4-(3-isopropylamino-2-oxopropoxy)-1,2,5-thiadiazole, 3-ethyl-4-(3-isopropylamino-2-oxopropoxy)-1,2,5-thiadiazole, 3-ethyl-4-(3-tert-butylamino-2-oxopropoxy)-1,2,5-thiadiazole, 3-ethyl-4-[3-(1,1-dimethyl-2-hydroxyethylamino)-2-oxopropoxy]-1,2,5-thiadiazole, 3-ethoxy-4-(3-isopropylamino-2-oxopropoxy)-1,2,5-thiadiazole, 3-ethoxy-4-(3-tert-butylamino-2-oxopropoxy-1,2,5-thiadiazole, 3-ethoxy-4-[3-(2,2-dimethylpropylamino)-2-oxopropoxy]-1,2,5-thiadiazole, 3-phenyl-4-(3-isopropylamino-2-oxopropoxy)-1,2,5-thiadiazole, 3-phenyl-4-(3-tert-butylamino-2-oxopropoxy)-1,2,5-thiadiazole and 3-benzyl-4-(3-tert-butylamino-2-oxopropoxy)-1,2,5-thiadiazole. Neither reference has disclosed any biological activity for the ketones, however.

It is an object of the present invention to provide novel hydrolytically sensitive precursors of the ketone precursors of the $\beta$-adrenergic blocking $\beta$-hydroxylamines which are readily converted to the active $\beta$-blockers in the iris-ciliary body by combined hydrolytic and reductive processes.

SUMMARY OF THE INVENTION

This and other objects are realized by the present invention which provides compounds having the formula:

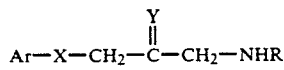

(I)

wherein —X— is —O—, —CH$_2$— or —; =Y is =O or a derivatized keto group, each of which is hydrolyzable or enzymatically convertible to a keto group; R is substituted or unsubstituted alkyl having from 1 to 12 carbon atoms or substituted or unsubstituted aralkyl having from 7 to 20 carbon atoms, said substituents not adversely affecting the β-adrenergic blocking and other pharmaceutical properties of the compound; and Ar is the residue of a 1-alkylamino-2-propanol having a cyclic substituent at the 3-position thereof, said substituted propanol having β-adrenergic blocking properties; and acid-addition salts thereof with pharmaceutically acceptable acids.

Another embodiment of the invention comprises a pharmaceutical composition in unit dosage form comprising an effective β-adrenergic blocking amount of one of the above described compounds or salts and a pharmaceutically acceptable carrier therefor.

A further embodiment of the invention comprises a method for treating a human or non-human animal in need thereof comprising administering to the animal an effective β-adrenergic blocking amount of one of the above described compounds or salts.

BRIEF DESCRIPTION OF THE DRAWINGS

The objects and advantages of the present invention will be apparent from the following detailed description and accompanying drawings, in which:

FIG. 2 is a plot of blood levels (µg/mL) of propranolone oxime vs. time following administration of propranolone oxime hydrochloride (6 mg/kg) to rats.

DETAILED DESCRIPTION OF THE INVENTION

Figure 1:
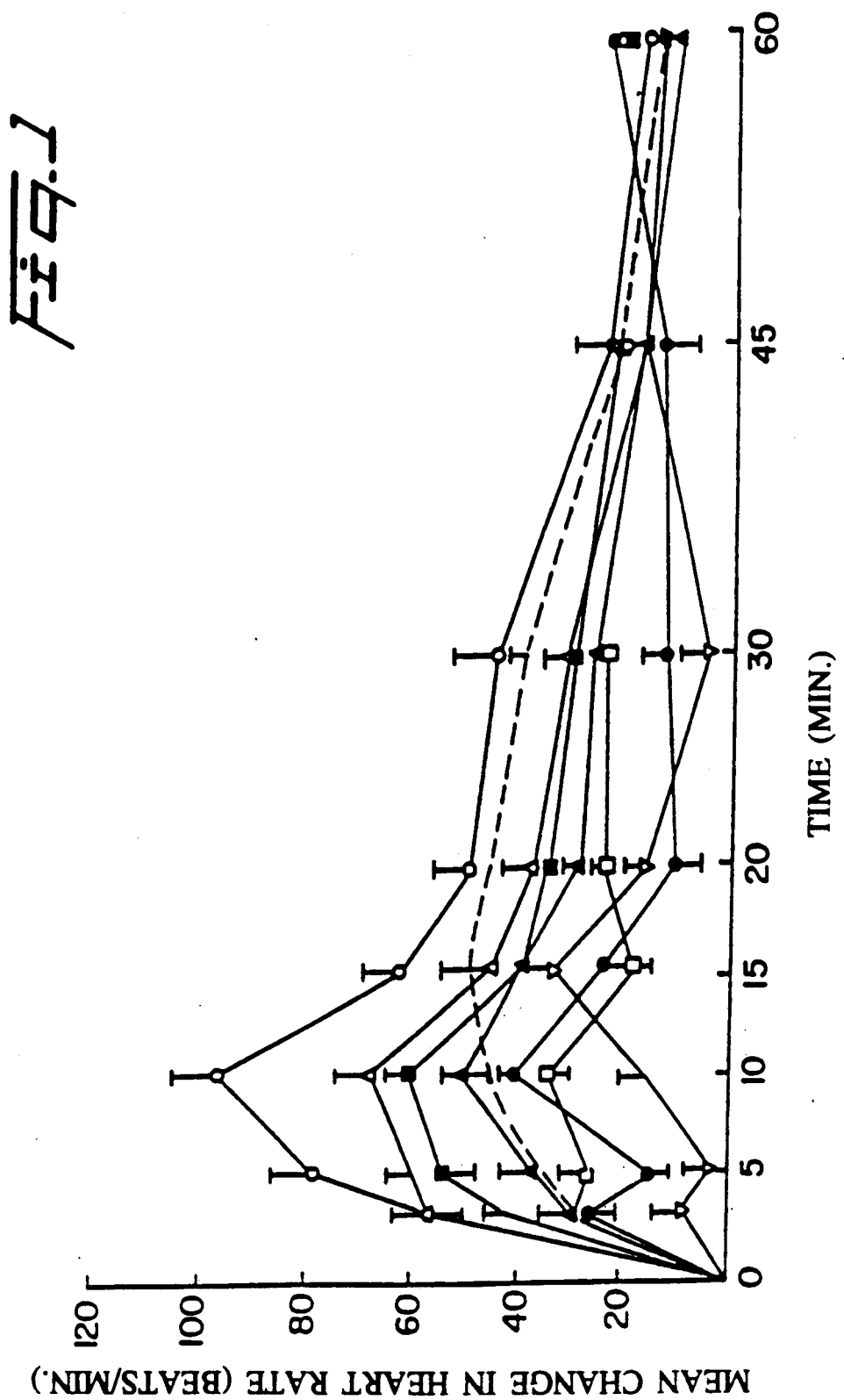
FIG. 1 is a plot of the mean change in heart rate with time following subcutaneous administration of isoproterenol (50 µg/kg) in rats pretreated with 6 mg/kg intravenous doses of representative ketoxime derivatives of this invention or of the corresponding known β-blockers.

The present invention is predicated on the discovery that the hydrolytically sensitive oxime-type and other labile ketone groups of the compounds of the invention would enable the delivery to and hydrolysis and reduction of the derivative at the iris-ciliary site of action to the active β-adrenergic blocking amino-alcohol.

The preferred compounds of the invention are those of the formula (I) above wherein =Y is =O, =N—OR$_1$, =N—NH$_2$, =N—NR$_1$R$_2$,

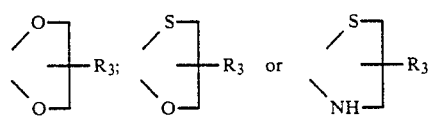

wherein R$_1$ and R$_2$ may be the same or different and are H, alkyl having from 1 to 8 carbon atoms, or aryl or aralkyl having from 6 to 15 carbon atoms; R$_3$ is R$_1$, —COOR$_1$ or —CON(R$_1$)$_2$ wherein R$_1$ is defined as above; and Ar and R have the meanings set forth above.

It will be understood, however, that =Y may be any group or substituent which is readily hydrolyzed or enzymatically converted to a ketone and then to a hydroxyl group at the intended site of action, preferably at the cornea or iris-ciliary body after administration of the parent compound to the animal undergoing treatment.

It is further preferred to employ those compounds of the above formula wherein R is a sterically hindered group such as the secondary or tertiary alkyls e.g., isopropyl, t-butyl, etc. Suitable aralkyl groups include benzyl, 3,4-dimethoxyphenethyl, 1-phenethylethyl etc.; it being understood that by the term "aralkyl" is intended any hydrocarbyl group.

Ar may be any aromatic or heterocyclic residue of the known 3-aromatic or 3-heterocyclic substituted 1-alkylamino-2-propanol β-blockers, e.g., those residues having the formulae:

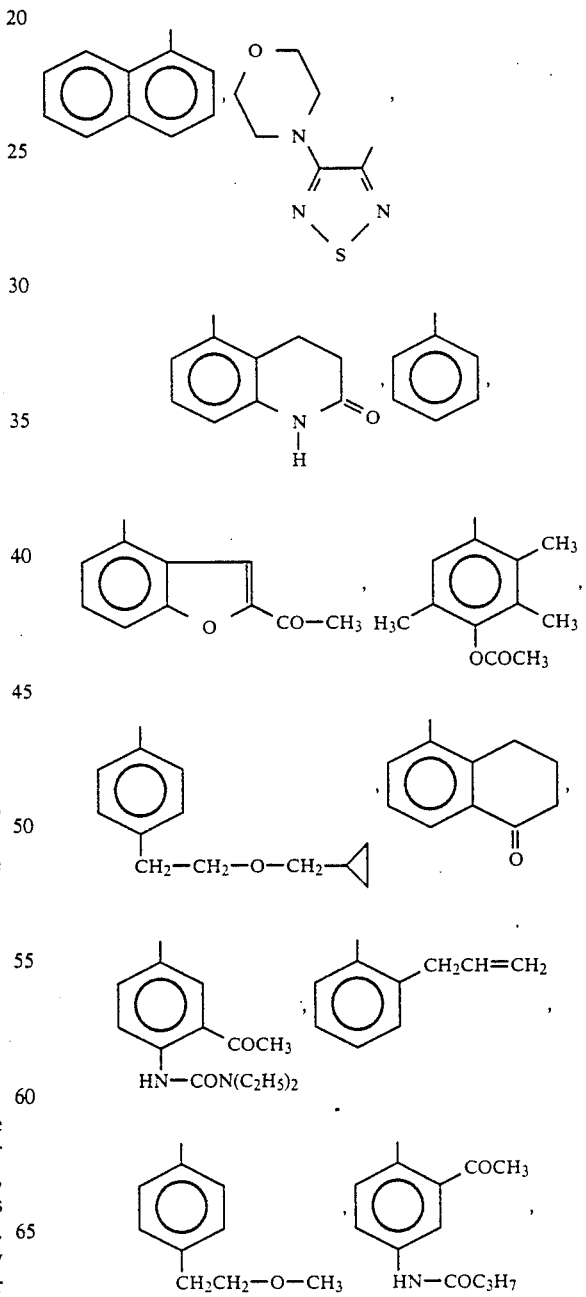

-continued

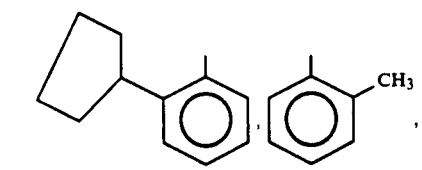

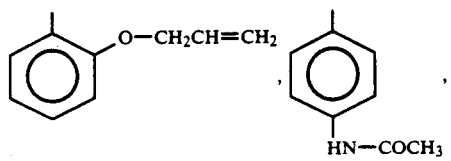

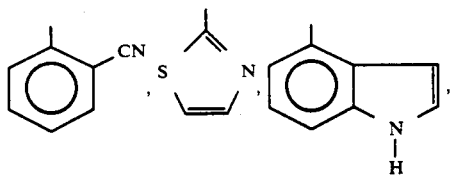

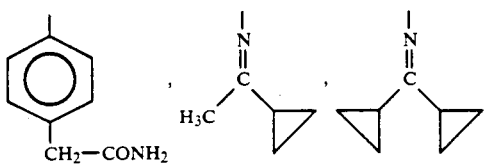

-continued

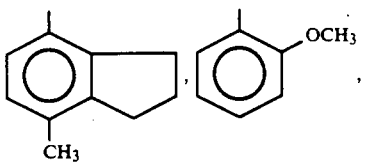

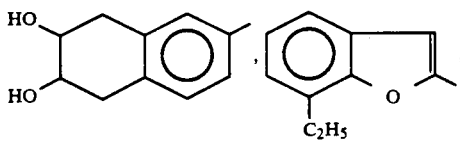

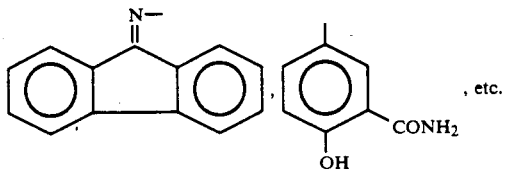
, etc.

Thus, Ar may be the residue of such known β-blockers as propranolol, timolol, carteolol, befunolol, metipranolol, betaxolol, bunolol, celiprolol, alprenolol, metoprolol, penbutolol, oxprenolol, bunitrolol, pindolol, atenolol, falintolol, ICI-118,551, moprolol, nadolol, bufuralol, IPS-339, labetolol and the like.

Any pharmaceutically acceptable acid may be used to form the acid addition salts of the invention, e.g., HCl, $H_2SO_4$, $H_3PO_4$, maleic, succinic, methanesulfonic, citric acid, oxalic acid etc.

The preferred compounds according to the present invention are those having the formulae in Table A.

TABLE A
$$\underset{\underset{Z=C}{\overset{\overset{OH}{|}}{\underset{|}{Z=CH}}\quad\quad\quad\underset{Z=C}{\overset{\overset{N-OH}{\|}}{}}}}{Ar-X-CH_2-Z-CH_2-NH-R}$$
| β-blocker No. | Name | Compound No. | Ar | R | X |
|---|---|---|---|---|---|
| 1 | Propranolol | Ia | 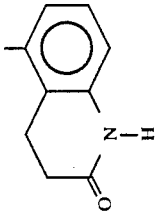 | —CH(CH$_3$)$_2$ | O |
| 2 | Timolol | Ib | 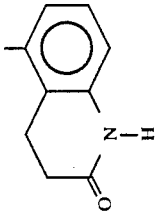 | —C(CH$_3$)$_3$ | O |
| 3 | Carteolol | Ic | 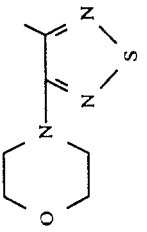 | —C(CH$_3$)$_3$ | O |
| 4 | I-i̇pr-Timolol | Id | 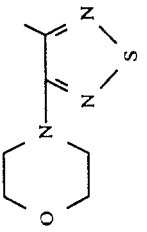 | —CH(CH$_3$)$_2$ | O |
| 5 | Alprenolol | Ie | 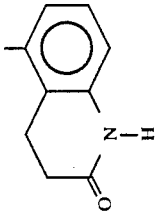 | —CH(CH$_3$)$_2$ | O |
| 6 | Atenolol | If | 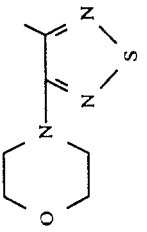 | —CH(CH$_3$)$_2$ | O |

TABLE A-continued
$$Ar-X-CH_2-Z-CH_2-NH-R$$
$$Z = CH \overset{OH}{|} \qquad Z = C \overset{N-OH}{\parallel}$$
| X | β-blocker No. | Name | Compound No. | Ar | R |
|---|---|---|---|---|---|
| O | 7 | Befunolol | Ig | 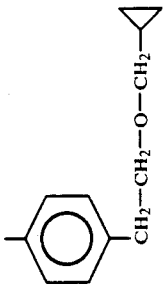 | —CH(CH$_3$)$_2$ |
| O | 8 | Betaxolol | Ih |  | —CH(CH$_3$)$_2$ |
| O | 9 | Bevantolol | Ii |  |  |
| O | 10 | Bufurolol | Ij | 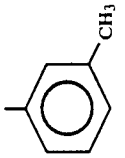 | —C(CH$_3$)$_3$ |
| O | 11 | Bunitrolol | Ik |  | —C(CH$_3$)$_3$ |
| O | 12 | Bupranolol | Il |  | —C(CH$_3$)$_3$ |

TABLE A-continued $$Ar-X-CH_2-Z-CH_2-NH-R$$
$$Z = C \overset{N-OH}{\underset{}{}}$$
$$Z = CH \overset{OH}{\underset{}{}}$$

| X | β-blocker No. | Name | Compound No. | Ar | R |
|---|---|---|---|---|---|
| O | 13 | Celiprolol | Im | 3-methyl-4-(HN-CON(C₂H₅)₂)-2-(COCH₃)-phenyl | —C(CH₃)₃ |
| O | 14 | Cetamolol | In | 2-(OCH₂CONHCH₃)-phenyl | —C(CH₃)₃ |
| O | 15 | Falintolol | Io | (1-methylcyclopropyl)-C(=N—) | —C(CH₃)₃ |
| O | 16 | ICI-118,551 | Ip | 4-methyl-7-methyl-indanyl | —C(CH₃)₃ |
| O | 17 | IPS-339 | Ir | fluoren-9-ylidene-N— | —C(CH₃)₃ |

TABLE A-continued $$\underset{\substack{Z=C \\ \|\\ N-OH}}{Ar-X-CH_2-Z-CH_2-NH-R}$$

| X | β-blocker No. | Name | Compound No. | Ar | R |
|---|---|---|---|---|---|
| O | 18 | Labetalol | Is | (4-CONH₂, 2-OH-phenyl) | —CH(CH₃)—CH₂CH₂—C₆H₅ |
| O | 19 | Levobunolol | It | (5-methyl-tetralin-1-one) | —C(CH₃)₃ |
| O | 20 | Mepindolol | Iu | (2-methyl-7-methyl-indol) | —CH(CH₃)₂ |
| O | 21 | Metipranolol | Iv | (2,3,5-trimethyl-4-OCOCH₃-phenyl) | —CH(CH₃)₂ |
| O | 22 | Metoprolol | Ix | (4-CH₂CH₂—O—CH₃-phenyl) | —CH(CH₃)₂ |

TABLE A-continued $$Ar-X-CH_2-Z-CH_2-NH-R$$

$$Z = CH(OH) \quad \text{or} \quad Z = C(N-OH)$$

| X | β-blocker No. | Compound No. | Name | Ar | R |
|---|---|---|---|---|---|
| O | 23 | Iy | L-Morprolol | 2-methoxyphenyl (o-OCH₃) | —CH(CH₃)₂ |
| O | 24 | Iz | Nadolol | 5,6,7,8-tetrahydronaphthalene-6,7-diol (HO, HO) | —C(CH₃)₃ |
| O | 25 | Iaa | Diacetyl-nadolol | 5,6,7,8-tetrahydronaphthalene-6,7-diyl diacetate (CH₃COO, CH₃COO) | —C(CH₃)₃ |
| O | 26 | Ibb | Oxprenolol | 2-(allyloxy)phenyl (—O—CH₂CH=CH₂) | —CH(CH₃)₂ |
| O | 27 | Icc | Penbutolol | 2-cyclopentylphenyl | —C(CH₃)₃ |
| O | 28 | Idd | Pindolol | 1H-indol-4-yl (N—H) | —CH(CH₃)₂ |

TABLE A-continued
$$\frac{Ar-X-CH_2-Z-CH_2-NH-R}{\substack{OH \\ | \\ Z=CH}} \qquad \substack{N-OH \\ \| \\ Z=C}$$
| X | β-blocker No. | Name | Compound No. | Ar | R |
|---|---|---|---|---|---|
| O | 29 | Pivaloyl Pindolol | Icc | 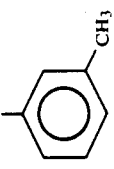 | —CH(CH$_3$)$_2$ |
| O | 30 | Solalol | Iff |  | —CH(CH$_3$)$_2$ |
| O | 31 | Toliprolol | Igg | 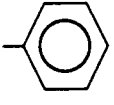 | —CH(CH$_3$)$_2$ |
Particularly preferred are compounds Ia, Ib, Ic, Ih, Il, Icc, Ik, Ip, It, Iv, Ibb, Ii, Ix and Is.

The following overall reaction scheme may be employed to prepare the products of the invention:

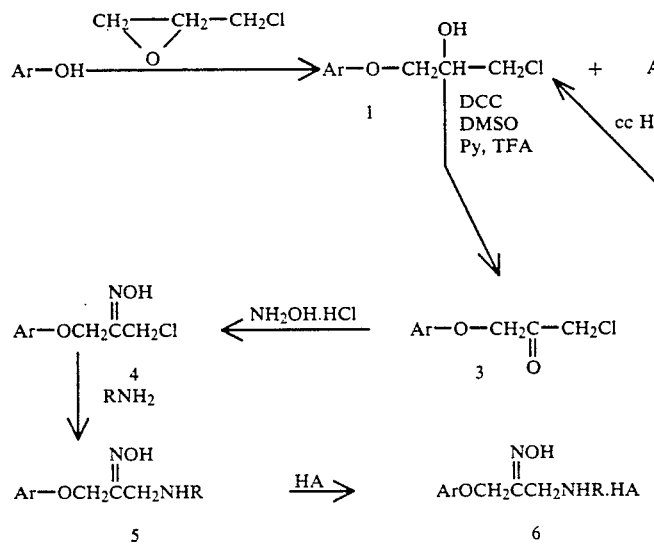

The conventional reaction of Ar—OH and epichlorohydrin with a small amount of morpholine as catalyst affords a mixture of the chlorohydrin 1 and the epoxide 2; the latter being converted to 1 by treatment with conc. HCl. Oxidation of 1 by the Pfitzner-Moffat method [Pfitzner et al, 1965, *J. Am. Chem. Soc.*, 87, 5661 and 5670] yields the ketone 3. Subsequent reaction of 3 with hydroxylamine HCl gives the oxime 4, which is a mixture of the Z- and E-isomers. In the usual case the ratio is about 2:1 (originally assumed Z:E, but later found to be E:Z, as discussed in more detail hereinbelow), as determined by NMR [Silverstein, "Spectrometric identification of organic compounds", 1974, 3rd ed.: G. Clayton Bassler and Terence C. Morril, New York, Wiley]. Obviously, a substituted hydroxylamine such as $CH_3ONH_2$ will be used in place of hydroxylamine when $R_1$ in $=N:OR_1$ is other than hydrogen. Similarly, reaction of the ketone 3 with hydrazine or a substituted hydrazine ultimately affords the hydrazones of the invention. The process can be similarly modified to prepare the ketals, thioketals and thiazolides of the invention, as would also be apparent to one skilled in the art. Reaction of the ketone with ethylene glycol or other appropriate diol/glycol, in the presence of a suitable dehydrating agent thus ultimately affords the ketals; reaction of the ketone with 2-hydroxyethylene thiol (ethylene thioglycol) or the like, using an appropriate dehydrating agent, ultimately affords the thioketals; and reaction of the ketone with an appropriate thiazoline-forming reagent such as cysteine ethyl ester hydrochloride in the presence of a suitable organic base ultimately yields the thiazolidine derivatives of the invention. All of these reactions are well-known chemical methods; see, for example, U.S. Pat. Nos. 4,069,322, and 4,268,441. Obviously, when X in formula (I) is other than oxygen, a chloro or bromo alcohol analogous to 1 could be employed as the starting material in the reaction sequence.

The major product of the aforedescribed reaction with hydroxylamine hydrochloride, originally assigned the configuration 4 (Z-), can be isolated by recrystallization from benzene. Treatment of 4 with isopropylamine in THF gives the oxime 5 essentially as the pure isomer, originally assumed to be E-, which can be converted to the HCl salt 6. Alternately, the oxidation of the racemic β-blocker or either stereoisomer of the β-blocker

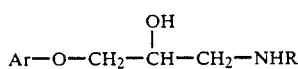

with DCC/(COCl)$_2$ at $-20°$ to $-78°$ C. will result in the ketone

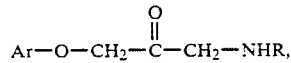

which can be converted to 6 without isolation by adding $H_2NOH\cdot HCl$.

The invention is illustrated by the following non-limiting examples wherein melting points were determined with a Fisher-Johns melting point apparatus and are uncorrected. The 90-MHz NMR spectra were taken on a Varian EM390 NMR spectrometer. TLC was performed on 0.25/mm Merck silica gel 60 F-254 glass plates. In these examples, the compounds of the invention are named as derivatives of 3-substituted-1-alkylamino-2-propanols. Alternatively, the compounds could be named as 1-substituted-3-alkylamino-2-propanol derivatives.

In Examples 1–4 which follow, indications of E- and Z-configuration are as originally assigned. A discussion of more recently developed and preferred procedures for preparing the compounds and corrected designations of configurations follows those examples.

EXAMPLE 1

The synthesis of the propanolone oxime 6a is a typical example.

1-(Isopropylamino)-3-(1-naphthyloxy)-2-propanone oxime HCl, Propranolone oxime hydrochloride 6a 3-Chloro-1-(1-naphthyloxy)-2-propanol 1a A mixture of 1-naphthol (20 g, 0.14 mole), ephichlorohydrin (51.3 g, 0.55 mole), and morpholine (0.7 mL) was heated at 100°–120° C. for 7.5 h. Excess epichlorohydrin and morpholine were removed under reduced pressure, the residue was dissolved in chloro-form and shaken with 10 mL of conc. HCl to convert 2a to the chlorohydrin 1a. The organic layer was separated and washed with water, then with dil. NaHCO₃ and finally with water. It was dried over anhydrous MgSO₄ and concentrated to yield 29.8 g (98%) of the crude product. This was used in the next step (oxidation) without purification.

Purification of a sample of the crude 1a was carried out by column chromatography (silica gel: Aldrich 100-200 mesh, 60 Å×4W, eluent CHCl₃). NMR (CDCl₃) δ 8.15 (m, 1H), 7.75 (m, 1H) 7.5-7.2 (m, 4H), 6.7 (d, d, J=7 Hz, J=1 Hz, 1H), 4.35-3.50 (m, 5H), 2.9 (d, J=6 Hz, 1H).

3-Chloro-1-(1-naphthyloxy)-2-propanone 3a

To a solution of 1,3-dicyclohexylcarbodiimide (DCC) (47.1 g), 0.228 mole DMSO (36 mL), and pyridine (3.6 mL) in diethyl ether (300 mL) was added a solution of 1a (18.0 g, 76 mmole) in diethyl ether (36 mL). To this solution was then added dropwise a solution of trifluoroacetic acid (1.8 mL) in diethyl ether under ice-water cooling, and the mixture was stirred at room temperature for 1 h and allowed to stand overnight. A solution of oxalic acid (18 g) in MeOH was added to the reaction mixture in small portions, and the stirring was continued for 0.5 h. The dicyclohexylurea was filtered and washed with ether. The filtrate was washed with a 5% NaHCO₃ solution, then with water and dried over anhydrous MgSO₄. From the filtrate, 6.3 g of the desired compound was recovered. The mother liquor was concentrated under reduced pressure and the residue was recrystallized from 2-propanol to yield an additional 3.3 g. The total yield was 9.6 g (56%). The product was used in the next step without further purification. A pure sample was obtained by column chromatography (silica gel: Aldrich 100-200 mesh, 60 Å×7W, eluent CHCl₃: hexane=3:1). NMR(CDCl₃) δ 8.25 (m, 1H), 7.80 (m, 1H), 7.65-7.20 (m, 4H), 6.75 (d, J=7 Hz, 1H), 4.83 (s, 2H), 4.43 (s, 2H).

3-Chloro-1-(1-naphthyloxy)-2-propanone oxime 4a

A mixture of 3a (1.0 g, 4.26 mmole), hydroxylamine hydrochloride (0.36 g, 5.1 mmole), and DMSO (10 mL) was heated at 40°-60° C. for half an hour. Water (40 mL) was introduced and the solution was extracted with CHCl₃. The organic layer was washed with water several times, dried over anhydrous magnesium sulfate, and concentrated under reduced pressure. The crude yield was 1.1 g (100%). Further purification was carried out by column chromatography (silica gel: Aldrich 100-200 mesh, 60 Å×30W, eluent:benzene:AcOEt=4:1). The product was a mixture of Z- and E- isomer (originally assumed Z:E=2:1). This isomer mixture could be used in the next step. NMR (CDCl₃+DMSO-d₆ as originally assigned (1 drop) δ 10.85 (s, 0.33H, —NOH of E-isomer), 10.75 (s, 0.67H, —NOH of Z-isomer), 8.4-8.1 (m, 1H), 7.9-7.65 (m, 1H), 7.6-7.2 (m, 4H), 6.95-6.7 (m, 1H), 5.2 (s, 1.33H, OCH₂ of Z-isomer), 4.9 (s, 0.67H, OCH₂ of E-isomer), 4.45 (s, 0.67H, —CH₂Cl of E-isomer), 4.3 (s, 1.33H, —CH₂Cl of Z-isomer).

What was originally assumed to be the Z-isomer was isolated from the crude product by recrystallization from benzene, m.p. 162°-163° C.

1-(Isopropylamino)-3-(1-naphthyloxy)-2-propanone oxime, Propranolone oxime 5a A mixture of 4a (2.5 g, 10 mmole), isopropylamine (6.0 g, 8.7 mL, 100 mmole), and THF (50 mL) was heated at 50° C. for 1.5 h. The reaction mixture was concentrated under reduced pressure. To the residue was added dil. NaHCO₃ and the solution was extracted with ethyl acetate. After the organic extract was shaken with dil. HCl solution, the separated aqueous layer was made basic with dil. HCl solution, extracted with AcOEt, dried over anhydrous MgSO₄ and concentrated under reduced pressure. The crude yield was 2.6 g (95%). The crude product was purified from a mixed solvent of isopropyl ether and hexane. The pure yield was 0.98 g (36%), m.p. 131.5°-132.5° C. This product was originally determined to be the E-isomer only. NMR(CDCl₃) δ 8.30-8.20 (m, 1H, one of H of naphthalene), 6.90-6.80 (m, 1H, one of H of naphthalene), 5.16 (2, 2H, —OCH₂—), 3.70 (s, 2H, —CH₂N—), 3.05-2.70 (m, 1H, N—CH<), 1.10.

1-(Isopropylamino)-3-(1-naphthyloxy)-2-propanone oxime hydrochloride, Propranolone oxime Hydrochloride 6a To diethyl ether saturated with HCl gas was added a solution of propranolone oxime 5a (0.30 g) in diethyl ether. The mixture was stirred at room temperature for 0.5 h. The precipitated white crystals were filtered and dried in vacuo overnight. The yield was 0.32 g (94%). This product was originally thought to be essentially pure E-isomer. NMR (DMSO-d₆) δ 12.00 (s, 1H, —NOH), 8.30-8.15 (m, 1H, of naphthalene), 7.95-7.80 (m, 1H, of naphthalene), 7.65-7.30 (m, 4H, part of naphthalene), 7.05-6.95 (m, 1H, one of H of naphthalene), 5.15 (s, 2H, —OCH₂), 3.96 (s, 2H, —CH₂N), 3.55-3.20 (m, 2H, NCH, —NH), 1.27 (d, J=6 Hz, 6H, —(CH₃)₂). Anal. (C₁₆H₂₀O₂N₂·HCl) C,H,N.

Propranolone oxime corresponds to the compound identified as Ia of Table A.

EXAMPLE 2

1-(tert-Butylamino)-3-[(4-morpholino-1,2,5-thiadiazol-3-yl)oxy]-2-propanone oxime oxalate, Timolone oxime oxalate 6b:

3-Chloro-1-[(4-morpholino-1,2,5-thiadiazol-3-yl)oxy]-2-propanol 1b was synthesized according to the method given for 1a. Yield 83%; the crude compound was used in the next step. NMR (CDCl₃) δ 4.5 (d, J=5 Hz, 2H), 4.2 (pentet, J=5 Hz, 1H), 3.8-3.65 (m, 6H), 3.55-3.40 (m, 4H). The peak of C—OH could not be identified.

3-Chloro-1-[(4-morpholino-1,2,5-thiadiazol-3-yl)oxy]-2-propanone 3b was synthesized according to the method given for 3a. Yield: 65%. The crude product was used in the next step. Purification of the crude product (recrystallization from 2-propanol) yielded the pure sample. NMR (CDCl₃) δ 5.22 (s, 2H), 4.13 (s, 2H), 3.75 (m, 4H), 3.50 (m, 4H).

3-Chloro-1-[(4-morpholino-1,2,5-thiadiazol-3-yl)oxy]-2-propanone oxime 4b

In a 500 mL round-bottomed flask were placed 3b (13.6 g, 49 mmole) and hydroxylamine hydrochloride (5.1 g, 73.4 mmole), in an ethanol-DMF mixed solvent (266 mL). The mixture was stirred at room temperature for 18 hours. The reaction mixture was poured into water (2L) and was extracted with ether. The organic extract was washed well with water, dried over anhydrous MgSO₄, and concentrated in vacuo at 30° C. The crude yield was 11.8 g (83%). The product was a mixture of Z- and E- isomers (Z:E=1.1: 1.0 as originally assigned). This crude mixture can be used in the next step. NMR (CDCl$_3$) as originally assigned δ 9.30 (broad s, 0.5H, —NOH of E-isomer), 9.10 (broad s, 0.5H, —NOH of Z-isomer), 5.35 (s, 1H, O—CH$_2$ of Z-isomer), 5.10 (s, 1H, E-isomer), 4.30 (s, 1H, —CH$_2$—N of E-isomer), 4.17 (s, 1H, —CH$_2$—N of Z-isomer), 4.8–4.7 (m, 4H), 3.6–3.4 (m, 4H).

1-(tert-Butylamino)-3-[(4-morpholino-1,2,5-thiadiazol-3-yl)oxy]-2-propanone oxime, Timolone oxime 5b In a 250 mL round-bottomed flask fitted with a dropping funnel was placed 4b (9.8 g, 33.5 mmol) in THF (147 mL). The solution was cooled in an ice bath, and a solution of tert-butylamine (12.2 g, 168 mmol), in THF (20 mL) was added through the dropping funnel during 10 minutes keeping the reaction temperature at −5° to 0° C. (pH 6–7). The stirring was continued for 1 hour at the same temperature. The solvent was evaporated under reduced pressure at 25° C. To the residue was added diluted HCl (2.8 mL conc. HCl) and it was extracted with ethyl acetate. To the aqueous layer separated was added a dil. NaHCO$_3$ solution (NaHCO$_3$ 3.1 g) at −5° C. (pH~6–7). It was extracted with ether to remove some impurities. Small amounts of NaHCO$_3$ (0.1–0.3 g) were added to the aqueous layer to make it slightly basic, and the mixture was extracted with ether. This procedure was repeated 4 times (pH was about 8) and another 3 times after raising the pH to about 9 with dil. NaOH solution. The organic extracts were combined, washed with water, dried over anhydrous MgSO$_4$ and concentrated in vacuo. Yield 3.1 g (28%). The crude product was triturated with isopropyl ether to yield 2.8 g. This was recrystallized from isopropyl ether to yield 1.8 g (16%) of pure compound.

1-(tert-Butylamino)-3-[(4-morpholino-1,2,5-thiadiazol-3-yl)oxy]-2-propanone oxime oxalate, Timolone oxime oxalate 6b In a 50 mL round-bottomed flask was placed a solution of oxalic acid (0.20 g, 2.22 mmole) in ether (10 mL). To this solution was added a solution of 5b (0.43 g, 1.3 mmole) in ether. The mixture was stirred at room temperature for 1 hour. The white non-hygroscopic crystals were filtered and dried in vacuo. Yield 0.53 g (97%), m.p. 165°–166° (dec.). NMR (CDCl$_3$) δ 5.3 (s, 2H), 3.9–3.7 (m, 4H), 3.6–3.4 (m, 6H), 1.1 (s, 9H). Anal. (C$_{18}$H$_{25}$O$_7$N$_5$), C,H,N.

Timolone oxime corresponds to the compound identified as Ib in Table A.

EXAMPLE 3

5-[3-(tert-Butylamino)-2-hydroxyimino)propoxy]-3,4-dihydrocarbostyril hydrochloride, Carteolone oxime HCl 6c 5-(3-Chloro-2-hydroxypropoxy)-3,4-dihydrocarbostyril 1c In a 250 mL round-bottomed flask fitted with a reflux condenser were placed 5-hydroxycarbostyril (15.0 g, 92 mmole), epichlorohydrin (34.2 g, 0.37 mole), morpholine (1.5 mL), and dioxane (90 mL). The mixture was refluxed for 16 hours, then it was concentrated in vacuo (20 mm/Hg) at 80°–90° C. To the residue was added 300 mL of 2N HCl, stirred for 15 minutes, then 0.8–1.0 L of ethyl acetate was added and the mixture was stirred vigorously for 0.5 hour. The organic layer was separated, washed well with water, then with dil. NaHCO$_3$ and was concentrated in vacuo. Yield: 19.9 g (85%). NMR (DMSO-d$_6$) δ 10.3 (s, 1H, —NH—), 7.25–6.50 (m, 3H, Ph), 4.20–3.60 (m, 5H, OCH$_2$CHCH$_2$Cl), 3.00–2.30 (m, 4H, —CH$_2$CH$_2$CO—).

5-(3-Chloro-2-oxopropoxy)-3,4-dihydrocarbostyril 3c was synthesized according to the method described for 3a. NMR (DMSO-d$_6$) δ 10.10 (s, 1H, —NH—), 7.20–7.00 (m, 1H, Ph), 6.65–6.50 (m, 2H, Ph), 4.95 (s, 2H, OCH$_2$), 4.70 (s, 2H, CH$_2$Cl), 3.0–2.8 (m, 2H, —C—CH$_2$CO—), 2.5–2.3 (m, 2H, —CH$_2$—C—CO—).

5-[3-Chloro-2-(hydroxyimino)propoxy]-3,4-dihydrocarbostyril 4c was synthesized similarly to the method given for 4b. NMR (DMSO-d$_6$) as originally assigned δ 11.88 (s, 0.3H, E- of NOH), 11.80 (s, 0.7H, Z- of NOH), 10.08 (s, 1H, —NH—), 7.30–6.50 (m, 3H, Ph), 4.93 (s, 1.4H, Z- of OCH$_2$, 4.73 (s, 0.6H, E- of OCH$_2$), 4.38 (s, 2H, Z & E- of CH$_2$Cl), 3.00–2.80 (m, 2H, C—CH$_2$—CO—), 2.65–2.40 (m, 2H, CH$_2$—C—CO).

5-[3-(tert-Butylamino)-2-(hydroxyimino)propoxy]-3,4-dihydrocarbostyril, Carteolone oxime 5c In a 100 mL round-bottomed flask fitted with a dropping funnel were placed 4c (2.0 g, 7.45 mmole) and THF (70 mL). The solution was cooled to 0° C. and a solution of tert-butylamine (0.82 g, 1.17 mL, 11.2 mmole) in THF was introduced through the dropping funnel. The mixture was stirred under cooling for 2 hours. To the reactive mixture was added a solution of oxalic acid (1.48 g, 16.4 mmole) in THF. The precipitate was filtered, triturated with water (600–700 mL) by stirring well for 15 minutes, and it was filtered again. The filtrate was extracted with ethyl acetate several times. The aqueous layer was cooled to 0° C., basified with a dil. NaHCO$_3$ solution (NaHCO$_3$, 0.81 g), and was immediately extracted with ethyl acetate. The extract was evaporated in vacuo (20 mHg) at 30° C. Yield: 0.63 g (28%). Recrystallized from i-propanol, the product was originally designated as the E-isomer, m.p. 177°–180° C. (dec.) NMR (DMSO-d$_6$) δ 11.0 (s, 1H), 10.1 (s, 1H), 7.3–7.1 (m, 1H), 6.7–6.5 (m, 2H), 4.9 (s, 2H), 3.3 (s, 3H contain NH), 3.0–2.8 (m, 2H), 2.6–2.3 (m, 2H), 1.05 (s, 9H).

5-[3-(tert-Butylaminno)-2-(hydroxyimino)propoxy]-3,4-dihydrocarbostyril Hydrochloride, Carteolone oxime hydrochloride 6c The free base 5c was converted to the hydrochloride salt 6c in ether with HCl gas, m.p. 167°–169° C. (dec.). Anal. (C$_{16}$H$_{24}$O$_3$N$_3$Cl) C,H,N.

Carteolone oxime corresponds to the compound identified as Ic in Table A.

EXAMPLE 4

1-(Isopropylamino)-3-[(4-morpholino-1,2,5-thiadiazol-3-yl)oxy]-2-propanone oxime hydrochloride 6d 1-(Isopropylamino)-3-[(4-morpholino-1,2,5-thiadiazol-3-yl)oxy]-2-propanone oxime 5d In a 200 mL round-bottomed flask were placed 3-chloro-1-[(4-morpholino-1,2,5-thiadiazol-3-yl)oxy]-2-propanone oxime 4b (3.53 g, 12.1 mmole), isopropylamine (3.56 g, 60.3 mmole), and THF (71 mL). The mixture was stirred at room temperature for 2.5 hours. The reaction mixture was concentrated in vacuo at room temperature. The residue was triturated with isopropyl ether and precipitated crystals were filtered with suction. The crystals were dissolved in dil. HCl solution. To the solution were added ether and NaHCO$_3$ in small portions under vigorous stirring conditions. The organic layer was washed with water and dried over anyydrous MgSO4, and concentrated in vacuo. Yield: 0.42 g (11.6%) from isopropyl ether.

1-(Isopropylamino)-3-[(4-morpholino-1,2,5-thiadiazol-3-yl)oxy]-2-propanone oxime Hydrochloride 6d The oxime 4b (0.25 g) was dissolved in ether and ether saturated with HCl was introduced dropwise into the solution. The mixture was stirred for 10 minutes, filtered and dried in vacuo overnight. Yield: 89%. Anal. ($C_{12}H_{22}N_5O_3SCl$) C,H,N.

This oxime corresponds to the compound identified as Id in Table A.

ELEMENTAL ANALYSES

1—1-(Isopropylamino)-3-(1-naphthyloxy)-2-propanone oxime hydrochloride, propranolone oxime hydrochloride 6a, $C_{16}H_{21}O_2N_2Cl$).

Calc.: C, 62.23; H, 6.85; N, 9.07. Found: C, 62.32; H, 6.89; N, 9.05.

2—1-(tert-Butylamino)-3-[(4-morpholino-1,2,5-thiadiazol-3-yl)oxy]-2-propanone oxime oxalate, timolone oxime oxalate 6b, $C_{15}H_{25}O_7N_5S$ $C_{13}H_{23}O_3N_5S$.-$(COOH)_2$ Calc.: C, 42.95; H, 6.01; N, 16.70. Found: C, 43.00; H, 6.04; N, 16.67.

3—5-[3-(tert-Butylamino)-2-(hydroxyimino)propoxy]-3,4-dihydrocarbostyril hydrochloride, carteolone oxime HCl 6c, $C_{16}H_{24}O_3N_3Cl$.

Calc.: C, 56.22; H, 7.08; N, 12.30. Found: C, 56.10; H, 7.13; N, 12.21.

4—1-(Isopropylamino)-3-[(4-morpholino-1,2,5-thiadiazol-3-yl)oxy]-2-propanone oxime hydrochloride 6d, $C_{12}H_{22}N_5O_3S$ Cl.⅓ $H_2O$.

Calc.: C, 40.27; H, 6.38; N, 19.57. Found: C, 40.54; H, 6.42; N, 19.46.

Further experimentation has found that oxidation of the known parent β-blockers, the aryl-substituted-β-aminopropanols, with "activated" dimethylsulfoxide (DMSO) provides a convenient "one-pot" method to synthesize the preferred oximes of formula (I), which may be referred to as aryl-substituted-β-aminoketooximes, without isolation of the frequently unstable ketones. Assignment of Z and E stereoisomers of the oximes of formula (I), based on $^1H$—and $^{13}C$—NMR studies, was made, correcting that originally based on $^1H$ studies alone. Spontaneous isomerization of the oximes has also been noted in these further studies, which are detailed below.

In these studies, oxidation of the known β-blockers of the formula $$Ar-X-CH_2-\overset{\overset{OH}{|}}{CH}-CH_2-NHR \qquad (II)$$

wherein Ar, X and R are as defined with formula (I), with DMSO-oxalyl chloride reagent was investigated. It was found that the electrophilic attack of the DMSO/(COCl)$_2$ reagent on the secondary alcohol moiety of (II) took place smoothly at both −40° C. and −70° C. To avoid the possibility of reaction at the secondary amine site, hydrohalide salts of (II) were used.

In fact, formation of the acyloxysulfonium reagent, obtained from the reaction of DMSO with (COCl)$_2$, proved to be faster at both temperatures than O-acylation of (II) by (COCl)$_2$; thus, solutions of salts of (II) and DMSO were treated with (COCl)$_2$, avoiding the need to prepare the reagent in advance. Decomposition of the intermediate alkoxysulfonium salts of the formula

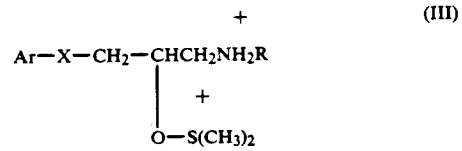

was best brought about by triethylamine (TEA). Deprotonation of (III) with any proton-containing base such as Amberlite ® (basic) ion-exchange resin or reaction in protic media resulted almost exclusively in reformation of (II). Interestingly, even slow (dropwise) addition of TEA brought about significant formation of (II), possibly because of the liberated secondary amine moiety in (III) acting as a nucleophile concurrently with TEA as proton scavenger.

The aryl-substituted aminoketones of the formula

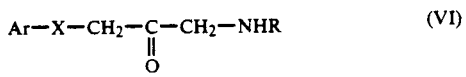

thus formed were found in certain cases to have very limited stability at temperatures at or above 0° C.; thus, they were preferably transformed in situ into the more stable ketonoxime derivatives of formula (I'), which have the structure

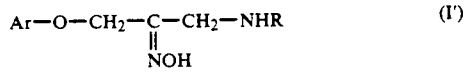

when X is O, as is the case for the preferred compounds of the invention. The oximes of the invention were isolated as their acid-addition salts (oxalates or hydrochlorides) as mixtures of stereoisomers in moderate to good yields. See Table B, Method A below.

A by-product isolated in significant yield in all cases proved to be the dione-dioxime. In some cases minor amounts of pyruvaldehydedioxime were also isolated. Formation of the dione-dioxime was virtually avoided and the yield of (I') was significantly enhanced when salts of (II) were exposed to DMSO/(COCl)$_2$ oxidation in the presence of excess acid (Table B, Method B) below.

Although DMSO-oxidation of $R^1R^2CH$—OH type alcohols is widely known, oxidation of an amine with an analogous structure ($R^1R^2CH$—NHR) has not been reported. In fact, DMSO-oxidation of simple secondary amines such as N-isopropyl-benzylamine and N-methylbenzylamine was attempted but failed.

Compounds (I') were isolated as mixtures of stereoisomers

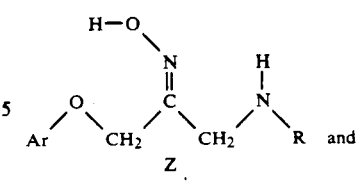

-continued

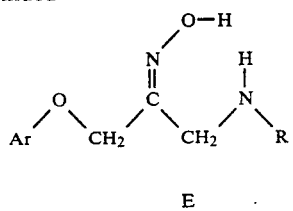

E in most cases, as indicated by their NMR spectra. The isomer ratio was estimated by ¹H—NMR and determined analytically by HPLC; see Experimental and Table B. Pure isomers of compounds (I') were isolated by fractional recrystallization or isomerization detailed later. Structural assignment of the stereoisomeric oximes (I') was based on their ¹H—NMR and ¹³C—NMR spectra. Configurational analysis of isomeric ketone oximes using NMR-techniques has been reported. In a systematic study of ¹H—NMR spectra of relatively simple ketone oximes (and other ketone derivatives), the shielding effects attributed to the lone pair of electrons on the N in the C=N bond have been established; see Karabatsos et al, *Tetrahedron* 24, 3347, 3923 (1968) and references cited therein. Thus, alpha-protons cis to the oximino-hydroxy group were found down-field relative to those in trans configuration [Karabatsos et al, supra; Saito et al, *J. Mol. Spectroscopy* 18, 1(1965); Saito et al, *J. Am. Chem. Soc.* 91, 6696 (1969)]. In the ¹³C—NMR spectra, on the other hand, the shielding effects were found to be the reverse; carbons cis to the oximino-O-atom appeared to be more shielded than the respective trans carbons, an effect interpreted as steric compression shift. See Levy et al, *J. Am. Chem. Soc.* 94, 4897 (1972); Hawkes et al, *J. Org. Chem.* 39, 1017 (1974); Bodor et al, *Tetrahedron* 35, 233 (1979). The ¹H—NMR spectra of compounds (I') (especially their salts) reflect only slight shielding effects on the OCH₂ and NCH₂ groups. These are inconclusive in most cases, and sometimes even controversial, inasmuch as the opposite assignation could be deduced from the ¹H—NMR data of some of compounds (I') and those of their respective salts (e.g. Ik and Il in Table C).

These discrepancies can probably be attributed to the secondary amine group, the protonation of which can strongly influence and occasionally outweight the shielding effects of the =NOH moiety. In the ¹³C—NMR spectra, on the other hand, this influence was not found; the same significant and conclusive shielding effects were observed on both the bases and salts (cf. Table D), allowing unequivocal assignment of the isomer with the more shielded OCH₂ and more deshielded NCH₂ as having the Z configuration. This assignment is also in agreement with that deduced from the ¹H—NMR spectra of the free bases (cf. Table C).

TABLE B

Physical data for oximes for formula (I').
Numbering of compounds is as in Table A hereinabove.

| | Salt | R' | Yield (%) method A | B | Solvent | M.P. °C. Z | E | T_R(min.) Z | E | % MeCN[h] |
|---|---|---|---|---|---|---|---|---|---|---|
| Ia | HCl | i | 68 | 64 | i-PrOH | 170–171[f,i] | 189–191[j] | 5.5 | 4.6 | 30 |
| | oxalate[a] | | 53 | | MeOH | | 152–158 | | | |
| Ie | HCl | i | 62 | 78 | MeCN | 118–120[k] | 154–156[l] | 5.6 | 4.7 | 30 |
| | oxalate[a,b] | | | 60 | MeCN | 142–145[a] | | | | |
| Ibb | HCl | i | 38 | 51 | i-PrOH | | 130–133[b,e] | 3.7 | 3.0 | 30 |
| | oxalate[b] | | 45 | | MeCN | 118–120[e] | | | | |
| Ix | HCl | i | 48 | 71 | MeCN | 129–131 | 164–168 | 7.1 | 5.3 | 20 |
| Ih | HCl | i | 60 | 82 | i-PrOH | | 168–170 | 5.7 | 4.7 | 30 |
| Icc | HCl | t | 39 | 62 | MeCN | | 179–181 | 7.0 | 6.1 | 40 |
| Ik | HCl | t | 55 | 52 | MeCN | | 189–191 | 5.9 | 4.0 | 20 |
| Il | HCl | t | 6[c] | 47[d] | MeCN | 164–166[g] | | 6.9 | 6.0 | 30 |
| Igg | HCl | i | 57 | 67 | i-PrOH | | 183–185 | 3.2 | 2.6 | 30 |
| Ii | HCl | dmp | 59 | 78 | i-PrOH | 155–158 | | 3.0 | 2.6 | 40 |

[a]Neutral salt (molar ratio 1:2);
[b]Acidic salt (molar ratio 1:1);
[c]From (II) base;
[d]Method C (see experimental);
[e]Z:E ratio 3:1;
[f]Base m.p. 127–129° C. (CCl₄);
[g]Base m.p. 162–164° C. (EtOH);
[h]% MeCN (v/v) in mobile phase; Mass Spectra - m/z (%):
[i]272 (6); 115 (100), 144 (73), 72 (62), 128 (56), 56 (53), 143 (48), 129 (40), 116 (36);
[j]272 (7), 115 (100), 129 (68), 144 (64), 143 (47), 72 (45), 56 (35), 183 (31), 116 (30);
[k]262 (10), 173 (100), 105 (92), 133 (65), 134 (60), 131 (59), 115 (49), 130 (42), 247 (38);
[l]262 (12), 105 (100), 173 (95), 133 (70), 72 (67), 131 (64), 134 (63), 130 (60), 115 (53).
*Structures of the Ar groups are given below.
i = i-Pr; t = t-Bu; dmp = 2-(3,4-dimethoxyphenyl)ethyl.
Structure of Ar groups in compounds of formula (I'):

Ia

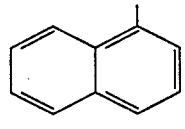

Icc

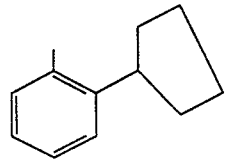

Ie

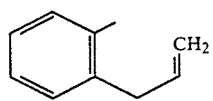

Ik

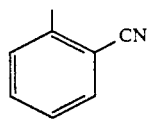

TABLE B-continued

Physical data for oximes for formula (I').
Numbering of compounds is as in Table A hereinabove.

Ibb 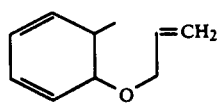   Il 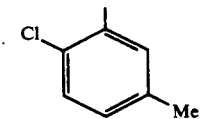

Ix 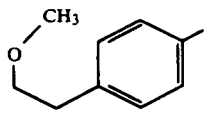   Igg 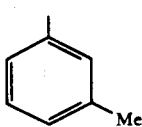

Ih 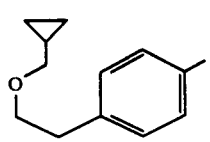   Ii 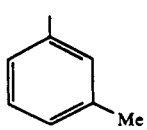

TABLE C $^1$H—NMR chemical shift data for Z and E stereoisomers of compounds of formula (I') in DMSO

|  |  | Z | | | E | | |
|---|---|---|---|---|---|---|---|
|  |  | NOH | OCH$_2$ | NCH$_2$ | NOH | OCH$_2$ | NCH$_2$ |
| Ia | HCl | 12.10 | 5.19 | 3.98 | 12.30 | 5.12 | 3.91 |
|  | base | 11.10 | 5.07 | 3.41 | 11.10 | 4.82 | 3.57 |
| Ie | HCl | 12.05 | 5.00 | 3.85 | 12.20 | 4.93 | 3.80 |
|  | base | 11.10 | 4.87 | 3.34 | 11.10 | 4.62 | 3.49 |
| Ibb | HCl | 11.95 | 4.98 | 3.85 | 12.20 | 4.87 | 3.85 |
|  | base | — | 4.91 | 3.22 | — | 4.63 | 3.33 |
| Ix | HCl | 11.97 | 4.94 | 3.80 | 12.20 | 4.85 | 3.80 |
|  | base | — | 4.90 | 3.19 | — | 4.55 | 3.31 |
| Ih | HCl | 11.97 | 4.94 | 3.75 | 12.20 | 4.87 | 3.80 |
|  | base | — | 4.90 | x | — | 4.56 | 3.31 |
| Icc | HCl | 11.98 | 4.98 | 3.75 | 12.20 | 4.94 | 3.75 |
|  | base | — | 4.94 | 3.35 | — | 4.66 | 3.46 |
| Ik | HCl | 12.10 | 5.20 | 3.80 | 12.30 | 5.26 | 3.80 |
|  | base | — | 5.08 | 3.40 | — | 4.89 | 3.50 |
| Il | HCl | 12.05 | 5.10 | 3.80 | 12.20 | 5.22 | 3.80 |
|  | base | 11.13 | 4.91 | 3.36 | — | 4.76 | 3.50 |
| Igg | HCl | 11.90 | 4.91 | 3.75 | 12.10 | 4.84 | 3.75 |
|  | base | — | 4.90 | 3.24 | — | 4.56 | 3.31 |
| Ii | HCl | 12.00 | 4.91 | 3.85 | 12.40 | 4.84 | 3.85 |
|  | base | — | 4.87 | 3.32 | — | 4.55 | 3.47 | x = overlapping signal.

TABLE D

Relevant $^{13}$C-NMR data of stereoisomers of formula (I') (#).

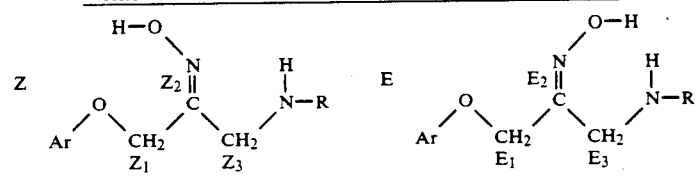

|  |  | Z$_1$ | Z$_2$ | Z$_3$ | E$_1$ | E$_2$ | E$_3$ |
|---|---|---|---|---|---|---|---|
| Ia | HCl | 61.47 | 148.50 | 42.58 | 67.49 | 147.32 | 37.27 |
|  | base | 61.08 | 154.25 | 46.32 | 67.55 | 154.78 | 40.96 |
| Ie | HCl | 61.32 | 148.53 | 42.38 | 67.26 | 147.41 | 36.96 |
|  | base | 61.09 | 154.30 | 46.26 | 67.28 | 154.77 | 40.88 |
| Ibb | HCl | 62.53 | 148.74 | 42.57 | 68.64 | 147.41 | 37.10 |
| Ix | HCl | 61.20 | 148.8 | 42.6 | 67.23 | 147.38 | 37.11 |
| Ih | HCl | 61.26 | 148.9 | 42.54 | 67.22 | 147.38 | 37.11 |
| Icc | HCl | 61.40 | 148.86 | 39* | 67.36 | 147.61 | 34.02 |
| Ik | HCl | 62.46 | 147.78 | 39* | 67.71 | 146.45 | 33.91 |
| Il | HCl | 62.07 | 148.24 | 39.67 | — | — | — |
|  | base | 61.62 | 154.5 | 42.41 | 68.0 | ** | 36.80 |
| Igg | HCl | 61.18 | 148.73 | 42.55 | 67.10 | 147.38 | 37.12 |
| Ii | HCl | 61.31 | 148.65 | 45.36 | 67.18 | 147.27 | 40.05 |

Structures of Ar, R given above (see Table B);
*overlap with DMSO-d$_6$ signals;
**not detected due to low solubility.

Spontaneous isomerization of HCl salts of compounds of formula (I') was also observed in solution; it was not observed in oxalates or bases of (I'). The isomerization of (I') was found to be facilitated in aprotic solvents, much slower in protic media and, especially, by addition of hydrochloric acid. Acid-catalyzed isomerization was in most cases found to result in formation of the opposite isomers in solutions and in suspensions, respectively. In suspension, clearly the less soluble isomer is forming. The isomeric equilibrium shifts towards the thermodynamically more stable isomer (Z in all cases) in solution, but towards the less soluble isomer (E in most cases; Z in Ia and Ii) in suspension. Probably due to insolubility, no isomerization of Il was observed.

EXPERIMENTAL

Melting points were determined on a Fisher-Johns melting point apparatus and are uncorrected. Compounds gave satisfactory microanalytical data for C, H, N (and Cl). $^1$H—NMR spectra were recorded on a Varian EM 390 (90 MHz) spectrometer, $^{13}$C—NMR spectra on a Varian VXR-300 FT spectrometer in DMSO-$d_6$ solutions with TMS and DMSO-$d_6$ internal standard, respectively. Mass spectra (EI) were recorded on a Kratos MS80RFA instrument operated at 70 eV electron energy and 200° C. source temperature.

SYNTHETIC METHODS

Method A

A solution of 3 mmol of the appropriate (II).HCl (oxalate in the case of the starting material for Ix) in 1.2-2.0 mL (17-28 mmol) of DMSO was diluted with 10 mL of dichloromethane and cooled to about −60° C. A solution of 0.37 mL (4.24 mmol) of oxalyl chloride in 5 mL of dichloromethane was added dropwise below −50° C. and stirring was continued for an additional 30-60 min. below −40° C. Precipitation occurred. The mixture was cooled below −60° C. again and a solution of 1.70 mL (12.25 mmol) of triethylamine was added at once. The temperature rose to about −40° C.; the precipitate dissolved. Then precipitation started again. The reaction mixture was stirred for an additional 1-1.5 hr. below −25° C., then a solution of 0.71 g (10 mmol) of hydroxylamine hydrochloride in 1 mL of water and 3 mL of ethanol was added. The temperature was allowed to rise to ambient, and the resulting clear solution was stirred for 6-18 hrs. at room temperature. It was then shaken with 60 mL of 5% sodium hydrogen carbonate solution; the water phase was extracted with ether, the combined organic phases were washed with water, dried over magnesium sulfate and evaporated below 30°-40° C. The remaining oil was dissolved in ether and acidified with ethereal hydrogen chloride (or, alternatively, with ethereal oxalic acid solution); the precipitated solid was filtered off, washed with ether and dried.

Method B

A solution of 3 mmol of the appropriate (II).HCl (oxalate in case of metoprolol, the starting material for Ix) in 1.2-2.0 mL (17-28 mmol) of DMSO was diluted with a solution of 0.1-0.2 g (1-2 mmol) of concentrated H$_2$SO$_4$ in 10 mL of dichloromethane and cooled to about −60° C. A solution of 0.38 mL (0.55 g; 4.35 mmol) of oxalyl chloride in 5 mL of dichloromethane was added dropwise below −50° C., and stirring was continued for an additional 40-50 min. below −40° C. Precipitation occurred. The mixture was cooled below −60° C. again and a solution of 2.0 mL (1.45 g; 14.35 mmol) of triethylamine was added at once. The temperature rose to about −35° C., the precipitate dissolved, then precipitation started again. The mixture was stirred for an additional 1 hr. at −25° to −45° C., then a solution of 0.7 g (10 mmol) of hydroxylamine hydrochloride in 1 mL of water and 3 mL of ethanol was added. The temperature was allowed to rise to ambient, and the resulting clear solution was stirred overnight at room temperature, then shaken with 60 mL of 5% sodium hydrogen carbonate solution. The aqueous phase was extracted with dichloromethane, the combined organic phases were washed with water, dried over magnesium sulfate and evaporated below 30°-40° C. The resulting oil was dissolved in ether and acidified with ethereal hydrogen chloride (or, alternatively, with ethereal oxalic acid solution). The precipitated solid was filtered off, washed with ether and dried.

Method C

A solution of 3.0 mL (42 mmol) of DMSO in 10 mL of dichloromethane was cooled to −60° C. A solution of 1.30 mL (14.9 mmol) of oxalyl chloride in 10 mL of dichloromethane was added dropwise while stirring and cooling to maintain the temperature below −45° C., and stirring was continued for 30 min. A solution of 1.5 g (15 mmol) of sulfuric acid in 10 mL of dichloromethane was then added and the mixture was stirred for 20 min. (precipitation occurred), followed by dropwise addition of 2.72 g (10 mmol) of bupranolol, dissolved in 10 mL of dichloromethane (all below −45° C.). Stirring of the thick slurry was continued for 40 min. below −45° C., then it was cooled to −70° C. and 7.0 mL (50 mmol) of triethylamine was added at once with vigorous shaking below −40° C. Stirring (and occasional shaking) of the thick reaction mixture was continued for an additional 1 hr., then a solution of 2.1 g (30 mmol) of hydroxylamine hydrochloride in 3 mL of water and 10 mL of ethanol was added at −20° C. The reaction temperature was allowed to rise to ambient, and the mixture (containing some undissolved material) was stirred overnight, then it was shaken with 100 mL of 5% sodium hydrogen carbonate solution. The precipitated solid was filtered off, washed and dried to give 0.55 g (20%) of Il.

The two-phase filtrate was separated, the water phase was washed with dichloromethane, the combined organic phases were washed with water, dried and evaporated. The solid residue was taken up with ether, filtered, washed and dried to give a further 1.50 g (40%) of Il. The two fractions of Il thus obtained were combined, dissolved in 50 mL of warm methanol, and the solution was acidified with ethereal hydrochloric acid and evaporated in vacuum. The residue was taken up with ethyl acetate, filtered, washed and dried to give 1.50 g (78%, 47% overall) of Il.HCl. Data for compounds of formula (I') are listed in Tables B-D.

High-performance liquid chromatography (HPLC)

HPLC separation of the Z and E isomers of compounds of formula (I') was carried out on a system consisting of a Spectra Physics (Palo Alto, CA) SP 8810 precision isocratic pump, SP 8780 autosampler equipped with a Rheodyne Model 7125 injector valve (20 μl sample loop), a SP 8450 UV/VIS detector operated at 254 nm, and an SP 4290 integrator. A 5 cm×4.6 mm i.d. Supelcosil LC-8-DB (5 μm) column (Supelco, Bellefonte, PA) was used. The mobile phase was a mixture of acetonitrile and an aqueous buffer solution containing 0.02M monobasic potassium phosphate (adjusted to pH=3.0 with concentrated phosphoric acid) and 0.01% (v/v) triethylamine. Acetonitrile proportions (% v/v) used in the mobile phase and retention time ($T_R$) data are given in Table B.

The following non-limiting examples illustrate the pharmacological properties of the compounds of the invention.

EXAMPLE 5

Effect on the Intraocular Pressure (IOP) of Rabbits

Adult male New Zealand albino rabbits weighing 2.5–3.5 kg were used. The animals were kept in individual cages with free access to food and water. Intraocular pressure was measured using a Digilab model 30R pneumatonometer. The pneumatonometer readings were checked at least twice a day using the Digilab calibration verifier. All measurements were obtained from unrestrained, unanesthetized rabbits. One drop of 0.5% propacaine (Ophthetic-Allergen Pharmaceuticals, Inc.) diluted 1:2 with saline was instilled in each eye immediately prior to IOP measurement. Drugs were administered as 1 or 2.5% solution in buffer pH 7.4 or in saline in both eyes of a group of at least four rabbits. Another group of at least three rabbits served as control and was administered the carrier only. IOP was recorded after 30 and 60 minutes and then after 2, 3, 4, 6 and 8 hours following the drug or carrier administration. Values are given as means ± standard error (S.E.) of the mean. The significance of the change was determined using the student's t-test.

The animals were also observed for local action of the drugs on the eyes, e.g., irritation, congestion, redness, lacrimation, etc.

The results are set forth in Tables 1–3.

TABLE 1

Effect of 1% solutions of propranolol.HCl 1a and propranolone oxime.HCl 6a on the IOP (mm/Hg) of rabbits.

| Time after administration | Propranolol HCl 1a, 1% | | | Propranolone oxime HCl 6a, 1% | | |
|---|---|---|---|---|---|---|
| | Control | Treated | % change after treatment | Control | Treated | % change after treatment |
| Zero | 28.8 ± 0.33 | 30.8 ± 0.40 | 0.00 | 29.3 ± 0.50 | 27.8 ± 0.62 | 0.00 |
| 30 min. | 32.0 ± 0.44 | 28.0 ± 0.56 | −9.10* | 28.2 ± 0.65 | 26.9 ± 0.58 | −3.23 |
| 60 min. | 32.7 ± 0.26 | 27.6 ± 0.62 | −10.39* | 29.1 ± 0.60 | 24.0 ± 0.60 | −11.51* |
| 2 hrs. | 31.3 ± 0.31 | 29.1 ± 0.38 | −5.52 | 27.7 ± 0.57 | 23.4 ± 0.51 | −15.82** |
| 3 hrs. | 30.8 ± 0.32 | 27.4 ± 0.54 | −11.04* | 26.3 ± 0.40 | 23.3 ± 0.35 | −16.18** |
| 4 hrs. | 29.9 ± 0.61 | 28.2 ± 0.48 | −8.44* | 26.8 ± 0.33 | 22.2 ± 0.42 | −20.14** |
| 6 hrs. | 30.8 ± 0.38 | 29.0 ± 0.45 | −5.84 | 28.8 ± 0.52 | 25.8 ± 0.56 | −7.08* |
| 8 hrs. | 30.7 ± 0.26 | 30.2 ± 0.43 | −1.95 | 29.2 ± 0.51 | 27.9 ± 0.62 | +0.50 |

*Significant decrease in I.O.P. ($P < 0.05$)
**Highly significant decrease in I.O.P. ($P < 0.01$)

TABLE 2

Effect of 2.5% solutions of propranolol.HCl 1a and propranolone oxime.HCl 6a on the IOP (mm/Hg) of rabbits.

| Time after Administration | Propranolol.HCl 1a (2.5%) | | | Propranolone oxime.HCl 6a (2.5%) | | |
|---|---|---|---|---|---|---|
| | Control | Treated | % change after treatment | Control | Treatment | % change after treatment |
| Zero | 26.6 ± 0.56 | 25.4 ± 0.56 | 0.00 | 25.8 ± 0.55 | 26.0 ± 0.48 | 0.00 |
| 30 min. | 28.0 ± 0.93 | 27.6 ± 0.56 | +8.66* | 27.2 ± 0.82 | 26.5 ± 0.63 | +1.92 |
| 60 min. | 26.6 ± 0.51 | 27.9 ± 0.60 | +9.84* | 26.2 ± 0.63 | 23.4 ± 0.55 | −10.00* |
| 2 hrs. | 24.6 ± 0.19 | 25.7 ± 0.55 | +1.18 | 26.3 ± 0.71 | 22.6 ± 0.43 | −13.08* |
| 3 hrs. | 25.6 ± 0.31 | 25.7 ± 0.39 | +1.18 | 26.7 ± 0.66 | 21.2 ± 0.28 | −18.46* |
| 4 hrs. | 25.2 ± 0.64 | 25.6 ± 0.46 | +0.79 | 26.8 ± 0.34 | 20.4 ± 0.34 | −21.54** |
| 6 hrs. | 26.4 ± 0.35 | 25.4 ± 0.54 | 0.00 | 25.9 ± 0.54 | 23.6 ± 0.48 | −9.23* |
| 8 hrs. | 26.0 ± 0.52 | 25.2 ± 0.68 | −0.79 | 26.0 ± 0.47 | 25.8 ± 0.65 | −0.77 |

*Significant change ($P < 0.05$)
**Highly significant change ($P < 0.01$)

TABLE 3

Effect of 1% solutions of timolol maleate 1b and timolone oxime oxalate 6b on the IOP (mm/Hg) of rabbits.

| Time after Administration | Timolol maleate 1b 1% | | | Timolone oxime oxalate 6b 1% | | |
|---|---|---|---|---|---|---|
| | Control | Drug-treated | % change after treatment | Control | Drug-treatment | % change after treatment |
| Zero | 28.72 ± 0.54 | 29.19 ± 0.78 | 0.00 | 28.72 ± 0.54 | 28.44 ± 0.63 | 0.00 |
| 30 min. | 26.62 ± 0.59 | 26.00 ± 1.23 | −10.93* | 26.62 ± 0.59 | 27.75 ± 0.68 | −2.43 |
| 1 hr. | 28.10 ± 0.85 | 27.25 ± 1.12 | 6.65 | 28.10 ± 0.85 | 24.30 ± 0.63 | −14.56** |
| 2 hr. | 27.02 ± 0.92 | 27.21 ± 0.58 | 6.78 | 27.02 ± 0.92 | 24.00 ± 0.44 | −15.61** |
| 3 hr. | 25.92 ± 0.44 | 25.00 ± 0.87 | 14.35** | 25.95 ± 0.44 | 25.13 ± 0.96 | −11.64** |
| 4 hr. | 26.45 ± 0.57 | 24.88 ± 1.00 | 14.77** | 26.45 ± 0.57 | 26.93 ± 0.48 | −5.31 |
| 5 hr. | 27.09 ± 0.55 | 24.25 ± 1.18 | 16.92** | 27.09 ± 0.55 | 26.88 ± 0.52 | −5.49 |
| 6 hr. | 27.88 ± 0.56 | 25.58 ± 0.85 | 12.37** | 27.88 ± 0.56 | 28.78 ± 0.91 | +1.20 |
| 8 hr. | 27.67 ± 0.63 | 26.33 ± 0.40 | 9.80* | 27.67 ± 0.63 | 26.33 ± 0.40 | −7.42 |

*Significant change ($P < 0.05$)
**Highly significant change ($P < 0.01$)

These results reveal that the ketoxime analogs of both propranolol and timolol display a certain degree of ocular hypotensive activity. Propranolone ketoxime 6a has shown the highest activity at both tested concentration levels, 1 and 2.5%. This activity was much more pronounced and prolonged than that of propranolol itself administered at the same dose levels (Tables 1 and 2). In addition, the ketoxime 6a was completely devoid of the ocular irritation which always accompanied propranolol administration at both dose levels. This irritant activity might have contributed to the reduced action of propranolol on the IOP at the 1% dose level and, also, might have completely masked its ocular hypotensive activity at the 2.5% dose level. Timolone ketoxime 6b has also shown a significant ocular hypotensive activity which was faster in its onset and shorter in its duration than timolol 1b itself (Table 3). On the other hand, the other ketoxime precursors, the ones for the N-isopropyl analog 6d of 6b, and 6c for carteolol, showed low activity at the dose levels used but showed some β-antagonist activity.

The unilateral administration of propranolol oxime hydrochloride 6a was subsequently studied at two different concentrations, 0.5% and 1.0%. Drugs were administered as 0.5% or 1.0% solution in saline in one of the eyes of each animal in a group of five rabbits. The untreated eye of each rabbit served as a control and received vehicle only. IOP was recorded as described above. Rabbits were also observed for any obvious manifestation of irritation caused by the drugs, such as congestion, redness and lacrimation. Significant decrease in the IOP was observed at both levels, only in the treated eye. No irritant action was noted.

EXAMPLE 6

Effect on Resting Heart Rate and on Isoprenaline-Induced Tachycardia in Rats

Groups of seven male Sprague-Dawley rats weighing 150-250 g were used. Each animal was anesthetized with sodium pentobarbital (50 mg/kg) and the jugular vein was cannulated with PE50 tubing. This cannula was subcutaneously threaded around the neck and exteriorized dorsally. The cannula was filled with heparin solution (1000/µl) and sealed with a solid 22-gauge stylet. Animals were housed in individual stainless steel cages and at least 24 hours were allowed for recovery from the surgery. Food and water were provided ad libitum. On the day of the experiment, the heart rate of each rat was monitored with a plethsmograph and the data recorded on a Physioscribe II recorder. One hour was allowed as an equilibration period before any drugs were administered. Drugs were dissolved in normal saline as 0.3% solution and were administered intravenously at a dose of 6 mg/kg. The resting heart rate was then recorded after 1, 3, 5, 10 and 15 minutes following i.v. injection. Isoprenaline (Isoproterenol bitartrate) was then administered subcutaneously at a dose of 50 µg/kg and the heart rate was recorded for 3, 5, 10, 15, 20, 30, 45 and 60 minutes after administration. A control group of seven animals was intravenously administered saline solution and was treated exactly in the same manner as the drug-treated groups.

The significance of the difference between the effect of saline solution and the drugs under investigation on the resting heart rate and on isoprenaline tachycardia was analyzed using the student's "t" test. Values are given as mean ±S.E. of the mean. The results are shown in FIG. 1, which depicts the mean change in heart rate over time for (☐) propranolol HCl, 1a; ▲ timolol maleate, 1b; (.) carteolol HCl, 1c; O propranolone ketoxime HCl, 6a; (▽) timolone ketoxime oxalate, 6b; (Δ) N-isopropyl timolone ketoxime HCl, 6d; ■ carteolone oxime HCl, 6c; and (---) saline solution.

In another set of experiments, the effect of the oral administration of propranolol HCl 1a and propranolone oxime HCl 6a in doses of 25, 50 and 100 mg/kg on the resting heart rate and isoprenaline-tachycardia was evaluated in rats. Drugs were administered to groups of 5 rats using a stomach tube and the heart rate was recorded for 1 hour. Then isoprenaline (50 µg/kg, s.c.) was administered and the heart rate was recorded after 3, 5, 10, 15, 20, 30, 45 and 60 minutes following administration. A control group of 5 rats was treated exactly in the same manner after the oral administration of the appropriate volume of saline solution.

The resting heart rate portions of these studies revealed that most of the tested ketoximes exhibit a negative chronotropic action in rats. Again, the ketoximes of propranol 6a and timolol 6b have shown the highest activity in this test, whereas carteolone ketoxime 6c and the oxime 6d were less active. It should be also noted that in this test carteolol itself 1c has shown the lowest activity on the heart rate of rats.

When the potential β-adrenergic antagonist activity of the ketoxime precursors of propranolol, timolol and carteolol was assessed against isoprenaline-tachycardia using the parent compounds as obvious reference drugs as described above, results were in agreement with the findings of the studies on effect on the IOP and resting heart rate. Thus, the ketoxime precursors of propranolol 6a and timolol 6b were the most effective whereas 6c and 6d were the least active. See FIG. 1.

These results indicate that at least two of the investigated ketoxime precursors 6a and 6b have an antiglaucoma activity which is probably linked to their β-adrenergic antagonistic properties. Yet, whether these properties are due to an inherent intrinsic activity of the ketoximes themselves or are the result of their active biological conversion to their parent drugs needed to be verified. For this reason the in vivo disposition of the different ketoximes and their parent β-blockers in the different ocular tissues was studied in rabbits.

EXAMPLE 7

In Vivo Distribution—Metabolism Studies

A. In Ocular Tissues of Rabbits

Adult male New Zealand albino rabbits weighing 2.5-3.5 kg were used. Standard doses of 100 µl of 1% solution of the drugs in saline solution were administered topically to both eyes of each rabbit. After appropriate time intervals (30, 60 and 120 minutes), the animals were sacrificed. Aqueous humor was obtained by making a single puncture at the limbus using a 25 g×⅝" needle attached to 1 cm$^3$ syringe. Then the cornea and the iris-ciliary body were isolated. The tissues were pooled and homogenized using a Tekmar SDT tissuemizer in ice cold perchloric acid (0.05M) which contained 0.05% sodium metabisulfite as antioxidant. Samples were then rehomogenized in $CH_3OH$ to prepare 10% homogenates, transferred to micro-filters and centrifuged for 20 minutes at 10000 r/minute to precipitate proteins. Aqueous humor was analyzed as such without any further dilution. Aliquots of 5-20 µl of the 10% tissue homogenate samples were analyzed by HPLC. Quantitation was done by using a calibration curve obtained by the addition of known amounts of the compound to aqueous humor, iris-ciliary body or cornea obtained from a control rabbit after topical administration of saline solution.

B. In Rat's Blood

A group of seven adult male Sprague-Dawley rats weighing 150-250 g was used. Animals were intrajugularly injected with propranolone oxime 6a at a dose of 6 mg/kg. After 1, 3, 5, 20, 40 and 60 minutes, one mL of blood was withdrawn from the jugular vein and dropped immediately into a tared tube containing 1 mL of ice-cold acetonitrile. The tubes were vigorously shaken, centrifuged, decanted and analyzed for propranolol 1a and propranolone oxime 5a by HPLC. Quantitation was done by using a calibration curve obtained by addition of known amounts of propranolol oxime HCl 6a to blood obtained from a control rat pretreated with saline solution.

The results of the ocular tissue tests are set forth in Tables 4 and 5.

TABLE 4

Tissue Concentration[a] of propranolol 1a and propranolone oxime 5a at various time intervals following topical administration of propranolone oxime HCl 6a, 1% solution.

| Tissue/ | Concentration of propranolone oxime 5a (mcg/g tissue) | | | Concentration of Propranolol 1a (mcg/g tissue) | | |
|---|---|---|---|---|---|---|
| Time | 30 min. | 60 min. | 120 min. | 30 min. | 60 min. | 120 min. |
| Cornea | 23.75 ± 4.91 | 16.40 ± 5.80 | 0.00 ± 0.00 | 1.68 ± 0.75 | 1.14 ± 0.29 | 1.14 ± 0.22 |
| Iris-Ciliary body | 7.79 ± 1.10 | 0.00 ± 0.00 | 0.00 ± 0.00 | 2.11 ± 0.29 | 1.79 ± 0.20 | 0.43 ± 0.11 |
| Aqueous humor | 0.82 ± 0.09 | 0.80 ± 0.06 | 0.00 ± 0.00 | 0.04 ± 0.02 | 0.71 ± 0.11 | 0.00 ± 0.00 |

[a]Figures represent the mean ± S.E. of the mean of at least 4 rabbits.

TABLE 5

Tissue Concentration[a] of propranolol at various time intervals following topical administration of propranolol.HCl 1a, 1% solution.

| | Concentration of propranolol (mcg/g tissue) | | |
|---|---|---|---|
| Tissue/Time | 30 min. | 60 min. | 120 min. |
| Cornea | 47.10 ± 5.57 | 14.54 ± 2.97 | 0.00 ± 0.00 |
| Iris-ciliary body | 8.05 ± 1.47 | 0.00 ± 0.00 | 0.00 ± 0.00 |
| Aqueous humor | 1.28 ± 0.19 | 0.26 ± 0.08 | 0.00 ± 0.00 |

[a]Figures represent the mean ± S.E. of the mean of four rabbits.

The results of the ocular tissue studies show that propranolol 1a could be detected in measurable concentrations in the different eye compartments for the first two hours following the topical administration of its ketoxime precursor 6a at its effective ocular hypotensive dose level of 1% (Table 4). On the other hand propranolol could not be detected in any of the tested eye tissues two hours after its ocular application (Table 5), and it had completely disappeared from the iris-ciliary body, which is supposed to be the site of its ocular hypotensive action, one hour after administration. These results might explain the shorter duration of propranolol action on the IOP relative to that of its ketoxime precursor. In addition, these results might also suggest that the ocular hypotensive activity of the oxime is most probably due to its active conversion to propranolol in situ in the ocular tissues of rabbits. This is also supported by the finding that following the ophtalmic administration of the other ketoxime precursors 6b and 6c of timolol and carteolol, respectively, at the low dose level used, the parent β-adrenergic antagonists could not be found in any of the eye compartments. This would suggest that either the ketone formed or the reduced form, the active β-blocker, is dosposed of so fast that it cannot be detected, or that the ketones are not such good substrates for the reductase enzyme as the propanolone ketoxime.

The studies in ocular tissue and blood revealed that the metabolic pathway of the oxime in the blood is quite different from that in ocular tissues. Thus, propranolol was not detected in rat's blood following the i.v. administration of the oxime and, instead, another more polar compound was detected. However, 5 minutes after injection even this compound had totally disappeared. The oxime itself appeared to have a very fast metabolism in blood. See FIG. 2, which is a plot of blood levels (μg/mL) of 5a vs. time after administration of 6a at a dose level of 6 mg/kg to rats. The $t_{\frac{1}{2}}$ in blood was equivalent to 7.64±0.55 minutes and one hour after i.v. administration the oxime had completely disappeared from the blood.

While these results would suggest that the propranolol formed in situ in the iris-ciliary body is responsible for the IOP reductions observed, the ketoxime itself might have intrinsic activity.

Based on the previous observation of the necessity to convert adrenalone to lipophilic esters to be reduced, one could expect that the lipophilic propranolone is easily reduced, while the ketones derived from timolol and carteolol, being less lipophilic (heterocyclic substitution of naphthalene), are not reduced that extensively. The N-isopropyl analog 6d of timolol was synthesized and tested in order to assess the importance of the N-alkyl function. Propranolol contains an i-propyl group, like 6d, but 6d was still found inactive at the selected dosage level. The difference in the behavior of 6a vs. 6b-d thus might be due to the difference in the Ar-group which appears to determine the substrate properties necessary to bind to the reductase enzyme. This hypothesis is supported by the relative HPLC retention times of the free bases 5a-5d which were 12.86, 7.22, 3.10, 6.10 for 5a, 5b, 5c and 5d, respectively, indicating that 5a is by far the most lipophilic.

The HPLC analytical method used to obtain these results is detailed below.

EXAMPLE 8

ANALYTICAL METHOD

A high pressure liquid chromatography (HPLC) method was developed for the assay of the β-blockers and their ketoxime analogs in biological fluids. The chromatographic analysis was performed on a system consisting of Beckman Model 112 solvent delivery system, Model 340 Injector, and Waters Model 481 variable wave length LC spectrophotometer. An ASI reverse phase chrompack $C_{18}$ column, operated at ambient temperature, was used for all separation. The mobile phase used for separation of propranolol 1a and propranolone oxime 5a consisted of water (90 mL), 1-heptanesulfonic acid (1g), 0.1M acetic acid (10 mL), 0.1M triethanolamine (100 mL) and methanol (799 mL). With a flow rate of 1.5 mL/minute, the two compounds showed retention times of 2.44 and 3.21 minutes for propranolone oxime and propranolol, respectively. The mobile phase used for separation of carteolol 1c, carteolone oxime 5c, timolol 1b, timolone oxime 5b and timolone isopropyl oxime 5d consisted of water (430 mL), 1-heptanesulfonic acid (2 g), 0.1M acetic acid (40 nL), tetrahydrofuran (30 mL), 0.1M triethanolamine (100 mL) and methanol (398 mL). With a flow rate of 1.5 mL/minute, the retention times for these compounds were 3.10, 3.54, 6.10, 7.22 and 9.15 minutes for carteolone oxime 5c, carteolol 1c, timolone isopropyl oxime 5d, timolone oxime 5b, and timolol 1b, respectively.

It is believed that the compounds of the invention are converted to their parent β-blockers according to the following scheme A which shows the conversion of 5a to 1a. Similar conversions would follow scheme B.

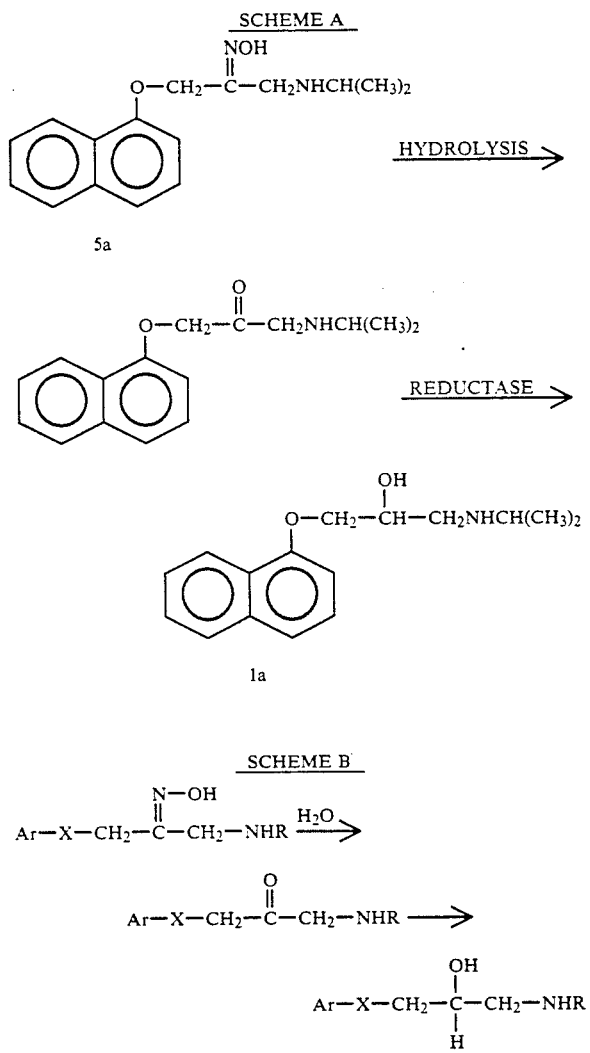

The hydrolytically sensitive precursors of the present invention comprise effective chemical delivery systems (CDS) for the β-blockers and intraocular pressure reducing agents.

The compounds of the invention may be administered to animals in need thereof by instilling solutions thereof into the eye or via oral tablets, capsules, etc., or any other convenient route of administration at dosages of from about 0.001 to about 20 mg/kg.

The compounds may be formulated with any conventional pharmaceutically acceptable carrier, such as those utilized for the parent amino-alcohol β-blockers.

Because the compounds of the present invention and their salts, most especially the oximes of formula (I') and the corresponding ketones to which they are hydrolyzed in the eye, have outstanding ability to reduce intraocular pressure when applied topically/locally to the eye, they are of particular use in the treatment of warm-blooded animals (human and non-human) with glaucoma and in the treatment of other warm-blooded animals (human and non-human) who require lowering of ocular pressure, such as animals with elevated intraocular pressure who may be at risk of developing glaucoma. The instant compounds and their salts can be conveniently administered for these purposes by formulating the selected free base or salt, in an effective intraocular pressure lowering amount, together with a non-toxic ophthalmically acceptable carrier therefor. Suitable carriers will be apparent to those skilled in the art of ophthalmic formulations. Obviously, the choice of suitable carriers will depend upon the exact nature of the particular dosage form desired, e.g. whether the compound of formula (I) or its salt is to be formulated into an ophthalmic solution or suspension (typically for use as eye drops), an ophthalmic ointment or cream or an ophthalmic gel; choice of carriers will also depend upon the particular compound of formula (I) or its salt chosen. Thus, for example, when a compound of formula (I) or salt in which =Y is =O is selected, if that ketone is unstable, care will be taken to utilize appropriate stabilizers in the formulation. The presently preferred compounds of formula (I), the oximes, i.e. those compounds in which =Y is =NOH and their salts, are in general sufficiently stable for formulation without special stabilizers. Preferred dosage forms are solutions, which contain a major amount of water in addition to the active ingredient. Minor amounts of other ingredients such as pH adjusters (e.g. a base such as NaOH), emulsifiers or dispersing agents, buffering agents, preservatives, wetting agents and jelling agents (e.g. methylcellulose) may also be present. Most preferably, the ophthalmic composition is a sterile, isotonic, buffered aqueous solution. Generally speaking, the ophthalmic composition containing a compound of formula (I) or its salt may be prepared and may contain the various inert ingredients or carriers previously described in the patent or non-patent literature as being suitable for ophthalmic compositions comprising known β-blockers such as timolol and labetolol. The amount of the free base or salt of this invention which will be present in the ophthalmic composition will of course vary with the particular CDS employed and the type of formulation selected. Typically, the composition will contain 0.01 to 5% of a compound of formula (I), preferably 0.25 to 2.5. In other words, each mL of solution will typically contain 0.1 to 50 mg, preferably 2.5 to 25 mg, of the free base. The dose administered ophthalmically will be selected according to the particular compound employed and the size and condition of the animal, but in any event will be a quantity sufficient to cause a significant reduction in intraocular pressure.

Thus, the present invention provides site-specific action in the reduction of intraocular pressure, a beneficial effect in glaucoma treatment, by local administration of the compounds of formula (I), in particular the ketoxime analogues of known β-adrenergic receptor antagonists. The possible mechanism involves an enzymic hydrolysis-reduction sequence, and, indeed, the corresponding amino alcohols have been identified in the ocular tissues. It has now been found that the in vivo biotransformation proceeds via a ketone intermediate to the stereoselective formation of the β-adrenergic blocker by the subsequent enzymic reduction. These consecutive processes occur only in ocular tissues, providing a site- and stereospecific drug delivery.

The importance of this novel chemical delivery system may also be highlighted by the fact that enantiomers of 1-(isopropylamino)-3-(1naphthyloxy)-2-propanol, i.e. propranolol, a widely used β-blocker, differ in potency, pharmacological action, and metabolism. The S-(−)-isomer has been found to be about 100 times as potent as the R-(+)-enantiomer which is, in turn, metabolized faster than the S-form; see, for example, Howe et al, *Nature* 210, 1336–1338 (1966); Barrett et al, *Br. J. Pharmacol.* 34, 43–55 (1968); Kawashima et al, *J. Pharmacol. Exp. Ther.* 196, 517–523 (1976); Von Bahr et al, *J. Pharmacol. Exp. Ther.* 222, 458–462 (1982); Silber et al, *J. Pharm. Sci.* 71, 699–703 (1982); Walle et al, *Br. J. Clin. Pharmacol.* 18, 741–747 (1984); and Nelson, *Drug Metab. Dispos.* 14, 506–508 (1986). The therapeutic formulation does, however, contain the racemic drug [*The United States Pharmacopeia, 21st Rev./The National Formulary*, 16th Ed., 907–908 (United States Pharmacopeia Convention, Inc., Rockville, Md., 1984)]. It is believed that the intraocular pressure lowering/β-adrenergic blocking feature of related substances is also connected to the chirality of the compounds, the S-(−)-isomer generally being the active enantiomer in terms of β-blocking activity as well as intraocular pressure lowering activity.

Enzymes capable of hydrolyzing oximes and making the resultant ketone available to further metabolic changes have been described in living organisms [Seaman, *Biochim. Biophys. Acta* 26, 313–317 (1957)]. Carbonyl reductases are a well-known family of NADPH-dependent oxidoreductases with similar physical and chemical properties which catalyze the reduction of aldehydes and ketones to the corresponding alcohol products (Wermouth, in *Enzymology of Carbonyl Metabolism 2: Aldehyde Dehydrogenase, Aldo-Keto Reductase, and Alcohol Dehydrogenase*, eds. Flynn and Weiner, 209–230, Liss, N.Y., 1985). The tissue distribution of carbonyl reductases appears to be widespread in mammals (liver, kidney, heart, brain, spleen, etc.), and they are expected to be present in ocular tissues. The iris-ciliary body is one of the major sites of the enzymatic activities in the eye. See Sichi et al, in *Extrahepatic Metabolism of Drugs and Other Foreign Compounds*, ed. T. E. Gram, 333–363, S. P. Medical and Scientific Books, New York, 1980; and Dos et al, *Exp. Eye Res.*, 33, 525–533 (1981).

To show that intraocular enzymes hydrolyze ketone precursors such as ketoximes, then further reduce the resultant ketone to an alcohol, the cornea was isolated from rabbit eye 0.5 hour after the topical administration (by instillation) of 1-(isopropylamino)-3-(1-naphthyloxy)-2-propanone oxime hydrochloride salt 6a in 1% (w/v) aqueous solution. The tissue was homogenized in an alkaline buffer (pH 10.0) to give 10% (w/v) homogenate, and extracted twice with equal volumes of methylene chloride/diethyl ether mixture (1:4, v/v) by shaking for 15 minutes. The organic layer was separated, then re-extracted with an equal volume of aqueous 0.1M hydrochloric acid solution. The aqueous phase was made alkaline (pH 10.0) and extracted with methylene chloride/diethyl ether, the organic layer was transferred to a deactivated glass vial, and the solvent was evaporated at reduced pressure under nitrogen stream. The residue was dissolved in 0.01M hydrochloric acid solution and analyzed by high-performance liquid chromatography (HPLC). A Supelcosil LC-8-DB analytical column (7.5 cm×4.6 mm i.d., 3 μm particle size) and mobile phase (1.5 mL/min flow rate) consisting of 30% acetonitrile in an aqueous buffer solution of 0.02M monobasic potassium phosphate (adjusted to pH 3.0 with phosphoric acid) and 0.01 (v/v) triethylamine. UV detection at 280 nm was applied. Peaks were identified as the E- and Z-isomers of the ketoxime administered, as the corresponding ketone 1-(isopropylamino)-3-(naphthyloxy)-2-propanone, and as the β-adrenergic antagonist 1-(isopropylamino)-3-(naphthyloxy)-2-propanol (propranol). The same experiment was carried out by administering 1-(isopropylamino)-3-(2-allylphenoxy)-2-propanone oxime hydrochloride salt in 2% (w/v) aqueous solution. The cornea extract showed the presence of the two oxime isomers, the corresponding ketone 1-(isopropylamino)-3-(2-allylphenoxy)-2-propanone, and the β-adrenergic blocker 1-(isopropylamino)-3-(2-allylphenoxy)-2-propanol (alprenolol). Authentic reference samples were used to identify the β-adrenergic blockers in the chromatograms, while the ketones were prepared by Pfitzner-Moffatt oxidation of these aminoalcohols, and characterized by HPLC and gas chromatography-mass spectrometry of their trifluoroacetyl derivatives.

It was then shown that reduction of 1-(isopropylamino)-3-(1-naphthyloxy)-2-propanone takes place in the iris-ciliary body. The compound was administered to the rabbit eye in propylene glycol/ethanol/pH=5.9 ophthalmic buffer (25:25:50 mixture, v/v) solution (concentration 0.5% hydrochloride salt, w/v). The iris-ciliary body was removed, extracted and analyzed 1.0 hour after the instillation of the compound, as described in the preceding paragraph. The enzymatic reduction product, 1-(isopropylamino)-3-(1-naphthyloxy)-2-propanol, i.e. propranolol, was clearly identified.

Finally, it was shown that the enzymatic reduction of the ketone is stereospecific. The extract residue from the iris-ciliary body of rabbit treated with 1-(isopropylamino)-3-(1-naphthyloxy)-2-propranolone oxime was reacted with the chiral reagent, 2,3,4,6-tetra-O-acetyl-β-D-glucoppyranosyl isocyanate, in acetonitrile and analyzed by the HPLC procedure of Sedman et al, *J. Chromatogr.* 278, 199–203, 1983 (Supelcosil LC-18 reversed-phase column of 7.5 cm×4.6 mm with 3 μm particles, mobile phase: 60% acetonitrile in 0.02M aqueous monobasic ammonium phosphate solution, 1 mL/min flow rate, UV detection at 254 nm). The sole presence of the S-(−)-enantiomer of 1-(isopropylamino)-3-(1-naphthyloxy)-2-propanol (propranolol) was established compared to the commercial racemic product.

In summary, high-performance liquid chromatographic analyses of eye compartments after local administration of the ketoxime analogs of the β-blockers propranolol and 1-(isopropylamino)-3-(2-allylphenoxy)-2-propanol (alprenolol) to rabbits have been carried out. Both the proposed ketone intermediates and the active aminoalcohols have been identified. The geometrical (Z- and E-) isomers of the oximes have been found to take up an equilibrium state during and after the distribution of the substance. This process is also catalyzed by enzymes present in the eye. Nevertheless, both oxime isomers yield the same hydrolysis product. The sequential nature of the formation of the active β-blocker is implied by the results obtained. Upon administering one of the ketones, 1-(isopropylamino)-3-(1-naphthyloxy)-2-propanone, which had been prepared by Pfitzner-Moffatt oxidation of propranolol, and isolated as the hydrochloride salt, the product of its enzymic reduction was apparently detected.

These studies have also revealed that only one enantiomer of the β-adrenergic blocker is present in the ocular tissues (viz. in the iris-ciliary body and cornea) at detectable levels, as shown for propranolol above. This has been assigned to be the more potent S-(−)-form, and these observations, together with the pharmacological data set forth hereinabove, support the explanation that the effect of the ketoxime derivatives is ultimately due to the biotransformation involving a hydrolysis - reduction sequence by intraocular enzymes, resulting in an optically active drug. The process is characteristic of the eye only; the systemic metabolism of these ketoximes proceeds by different routes. Consequently, a site- and stereospecific drug delivery has been accomplished by using this approach.

It can be seen from the foregoing that, in one of its most important aspects, the present invention provides a method for producing in the ocular tissue of a warm-blooded animal an effective intraocular pressure lowering amount of a β-adrenergic blocker of the formula

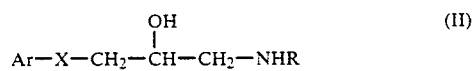

wherein —X— is —O—, —CH$_2$— or —; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties; said method comprising administering to the eye or eyes of said animal a quantity of a precursor of said β-adrenergic blocker of formula (II) which is bioconvertible in ocular tissue into said β-adrenergic blocker of formula (II) via the corresponding ketone intermediate of the formula

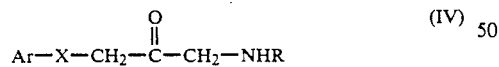

wherein Ar, X and R are defined as above, said quantity of said precursor being sufficient to result via the intermediate ketone in ultimate release of an effective intraocular pressure lowering amount of said β-adrenergic blocker of formula (II) in the ocular tissue of said animal.

While the ketoxime precursors of the invention, i.e. the compounds formula (I) herein wherein =Y is =NOH are preferred precursors for use in this method, the exact identity of the precursor is not critical. Indeed, the precursor may be any molecule which is bioconvertible in ocular tissue into the corresponding ketone of formula (IV), which can then be converted in those tissues to the desired active β-blocker of formula (II). Furthermore, the ketone of formula (IV) may itself be administered in accord with this method. The site-specificity of the subject method is of course a significant advantage thereof, for reasons discussed in the BACKGROUND OF THE INVENTION hereinabove. Moreover, the surprising finding of stereospecificity, such that the subject method results at least predominantly and, what is more likely, exclusively or almost exclusively in the more active enantiomer of the β-blocker of formula (II), provides a substantial advantage over the usual administration of the racemic mixture (half of which is, at best, inactive in lowering intraocular pressure and, at worst, exhibits undesired activities/toxicity and/or even interferes with the ability of the active enantiomer to exert the desired intraocular pressure lowering effect). This method is of particular interest as a means to the improved delivery into ocular tissue of known β-blockers such as propranolol, timolol, carteolol, befunolol, metipranolol, betaxolol, bunolol, celiprolol, alprenolol, metoprolol, penbutolol, oxprenolol, bunitrolol, pindolol, atenolol, falintolol, ICI-118,551, moprolol, nadolol, bufuralol, IPS-339, labetolol, bevantolol, bupranolol, cetamolol, levobunolol, mepindolol and toliprolol.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A compound having the formula

or a pharmaceutically acceptable acid addition salt thereof, wherein —X— is —O—, —CH$_2$— or —; =Y is a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties.

2. A compound or salt according to claim 1, wherein =Y is =N—OR$_1$, =N—NH$_2$, =N—NR$_1$R$_2$,

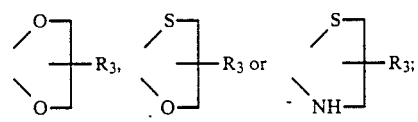

R$_1$ and R$_2$ may be the same or different and are H or alkyl having from 1 to 8 carbon atoms; and R$_3$ is R$_1$, —COOR$_1$ or —CON(R$_1$)$_2$ wherein R$_1$ is defined as above.

3. A compound or salt according to claim 1, wherein —X— is —O—.

4. A compound or salt according to claim 2, wherein —X— is —O—.

5. A compound or salt according to claim 1, wherein R is isopropyl.

6. A compound or salt according to claim 1, wherein R is t-butyl.

7. A compound or salt according to claim 1, wherein R is benzyl or 3,4-dimethoxyphenethyl.

8. A compound or salt according to claim 1, wherein Ar is

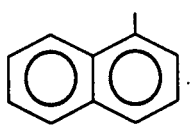

9. A compound or salt according to claim 1, Ar is

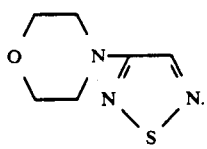

10. A compound or salt according to claim 1, Ar is

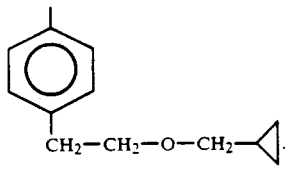

11. A compound or salt according to claim 1, Ar is

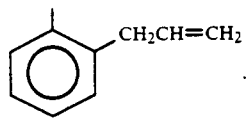

12. A compound or salt according to claim 1, wherein Ar is

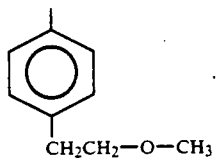

13. A compound or salt according to claim 1, Ar is

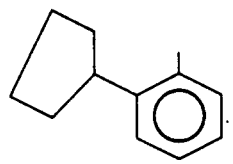

14. A compound or salt according to claim 1, wherein Ar is

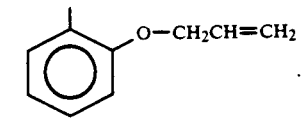

15. A compound or salt according to claim 1, wherein Ar is

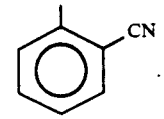

16. The compound of claim 1 having the formula

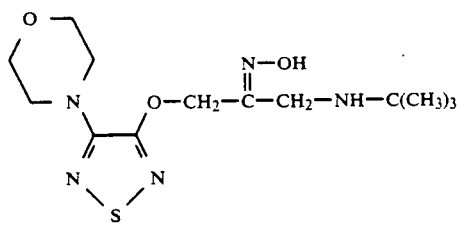

or a pharmaceutically acceptable acid addition salt thereof.

17. A method for eliciting a β-adrenergic blocking response in a warm-blooded animal in need thereof, which comprises administering to said animal an effective β-adrenergic blocking amount of a compound having the formula

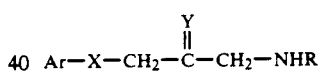

or a pharmaceutically acceptable acid addition salt thereof, wherein —X— is —O—, —CH$_2$— or —; =Y is a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties.

18. A method according to claim 17, wherein =Y is =NOH.

19. A method according to claim 17, wherein —X— is —O—.

20. A method according to claim 18, wherein —X— is —O—.

21. A method according to claim 17, wherein Ar is selected from the group consisting of

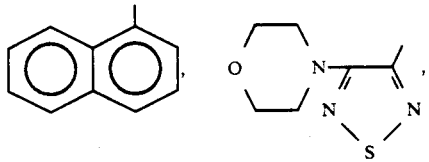

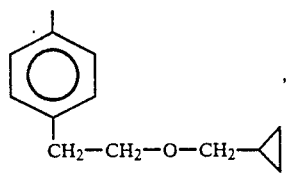, 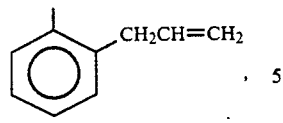,

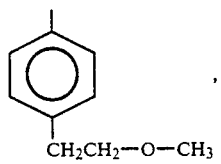, 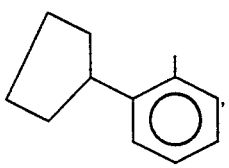,

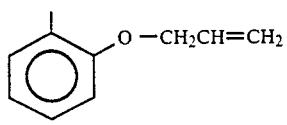 and 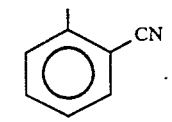.

22. A method according to claim 17, wherein the compound administered is selected from the group consisting of

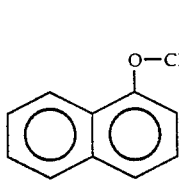,

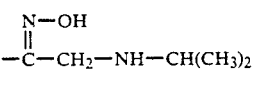,

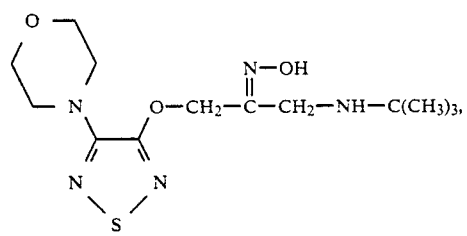,

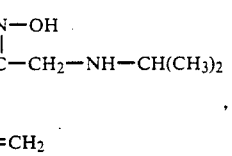,

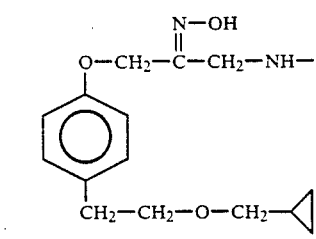,

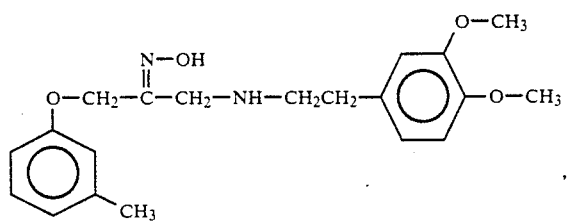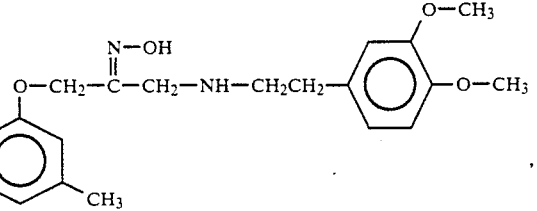,

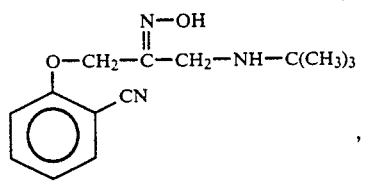,

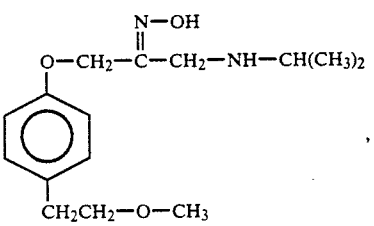,

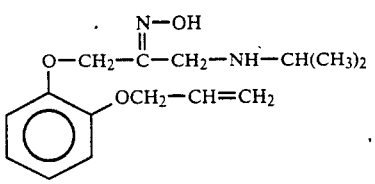,

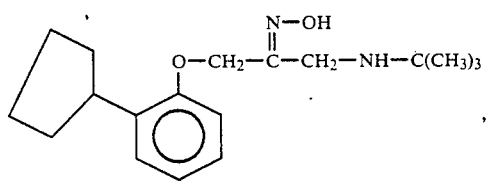,

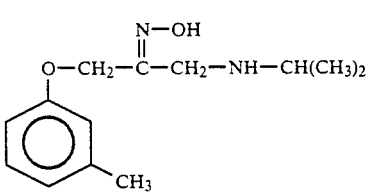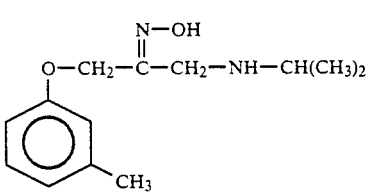 and

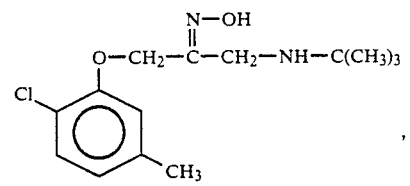, and the pharmaceutically acceptable acid addition salts thereof.

23. A pharmaceutical composition of matter, in unit dosage form, for use in eliciting a β-adrenergic blocking response in a warm-blooded animal, said composition comprising an effective β-adrenergic blocking amount of a compound having the formula

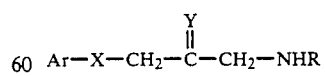 (I)

or a pharmaceutically acceptable acid addition salt thereof, wherein —X— is —O—, —CH$_2$— or —; =Y is a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties; and a non-toxic pharmaceutically acceptable carrier therefor.

24. A composition according to claim 23, wherein =Y is =NOH.

25. A composition according to claim 23, wherein —X— is —O—.

26. A composition according to claim 24, wherein —X— is —O—.

27. A composition according to claim 23, wherein Ar is selected from the group consisting of

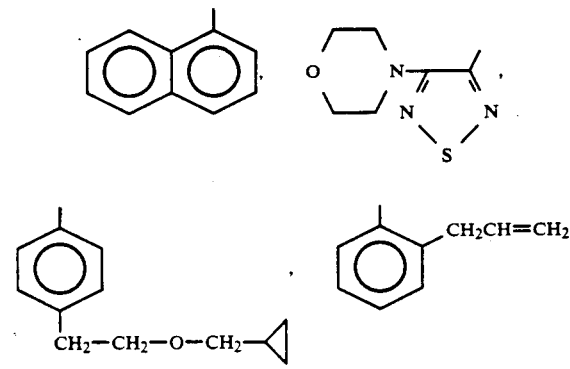

28. A composition according to claim 23, comprising an effective β-adrenergic blocking amount of a compound having the formula

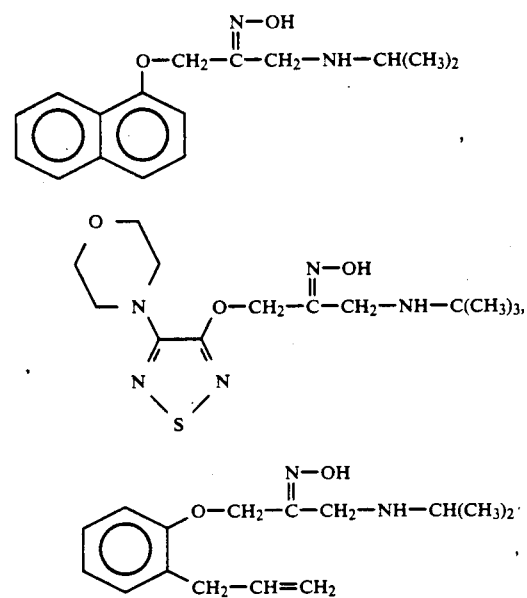

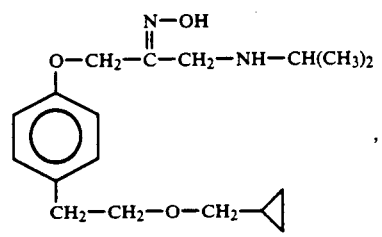

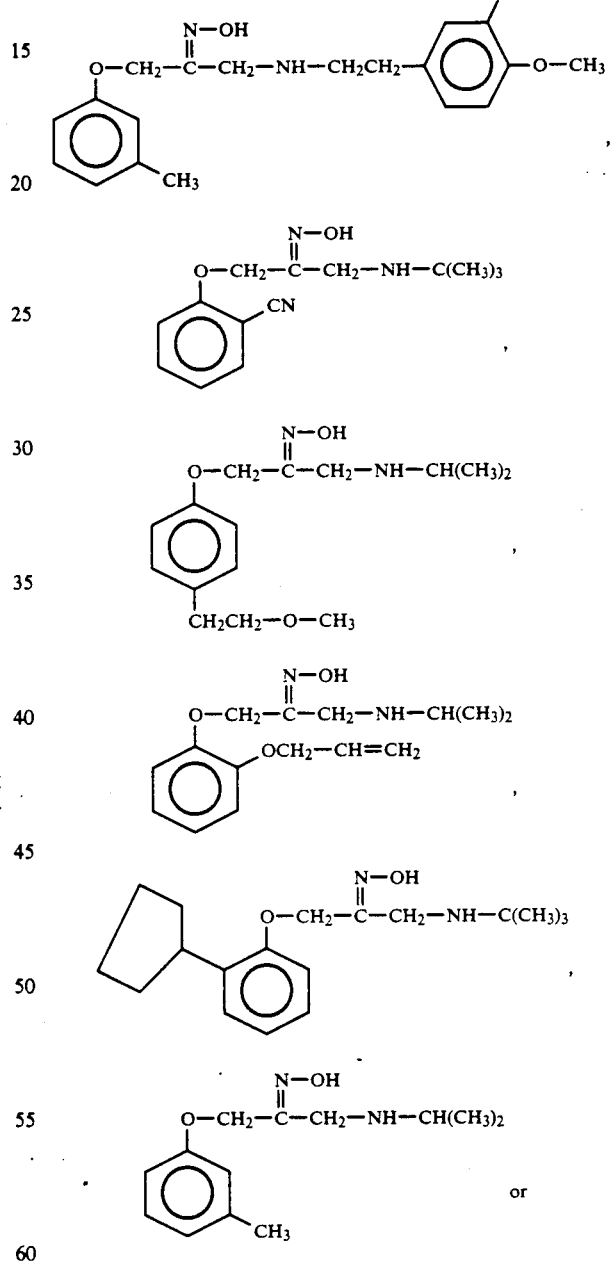

or

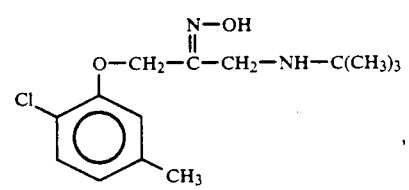

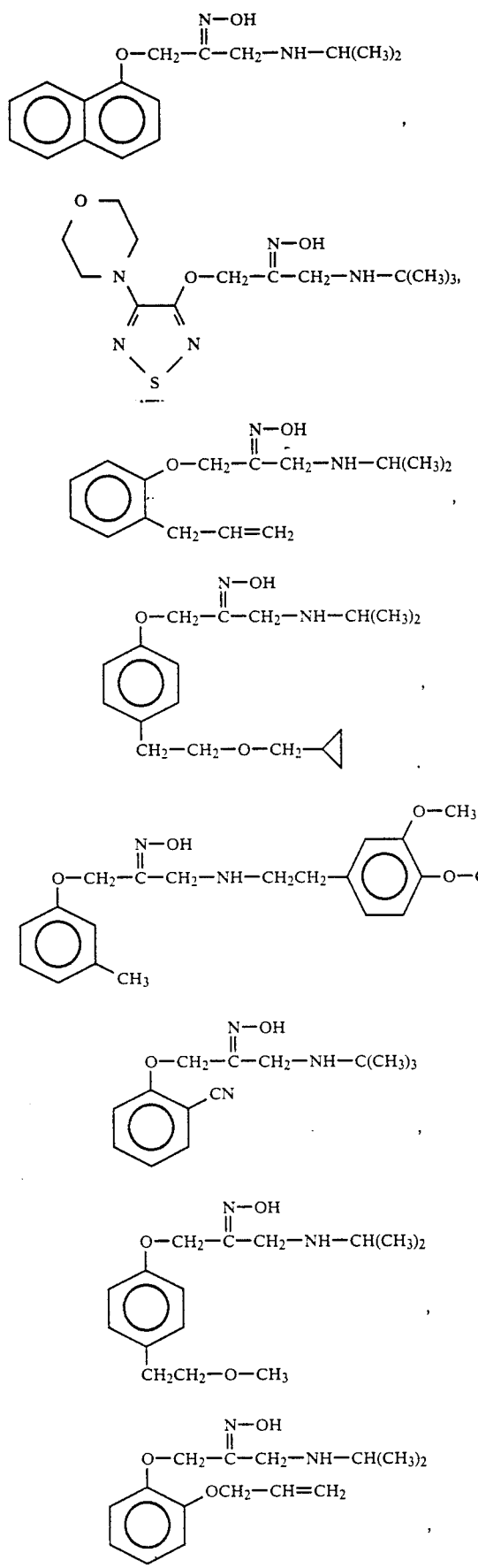

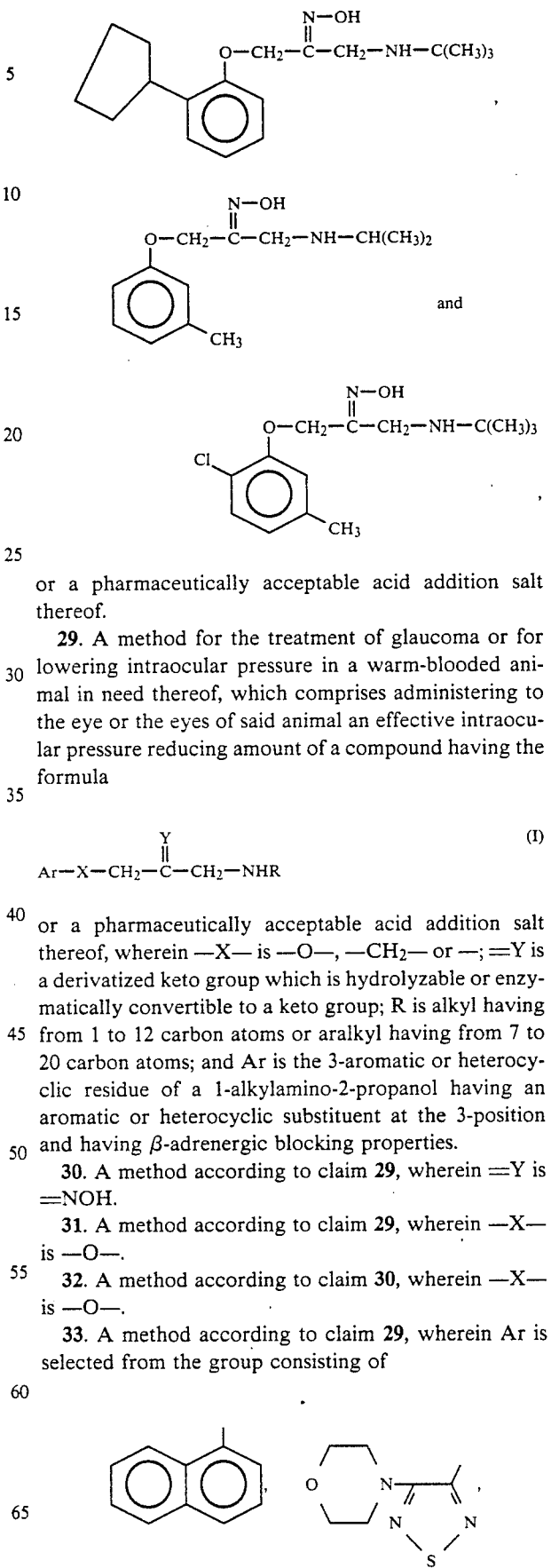

or a pharmaceutically acceptable acid addition salt thereof.

29. A method for the treatment of glaucoma or for lowering intraocular pressure in a warm-blooded animal in need thereof, which comprises administering to the eye or the eyes of said animal an effective intraocular pressure reducing amount of a compound having the formula $$Ar-X-CH_2-\underset{\underset{\|}{Y}}{C}-CH_2-NHR \qquad (I)$$

or a pharmaceutically acceptable acid addition salt thereof, wherein —X— is —O—, —CH2— or —; =Y is a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties.

30. A method according to claim 29, wherein =Y is =NOH.

31. A method according to claim 29, wherein —X— is —O—.

32. A method according to claim 30, wherein —X— is —O—.

33. A method according to claim 29, wherein Ar is selected from the group consisting of

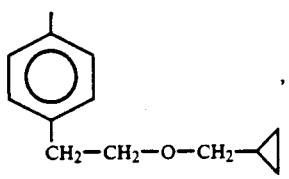 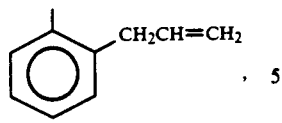

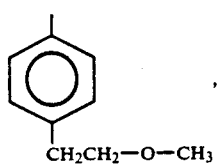 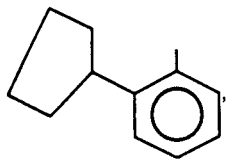

34. A method according to claim 29, wherein the compound administered is selected from the group consisting of

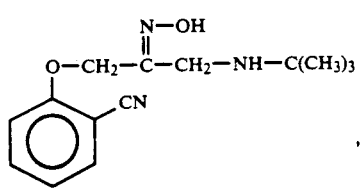

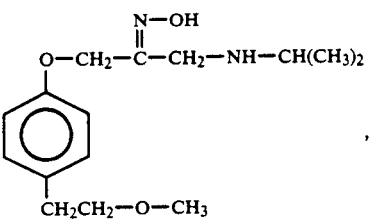

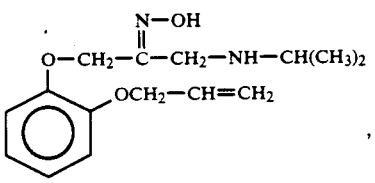

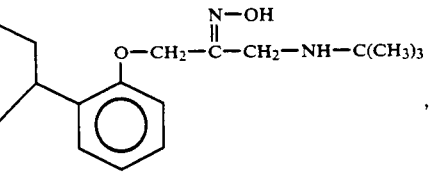

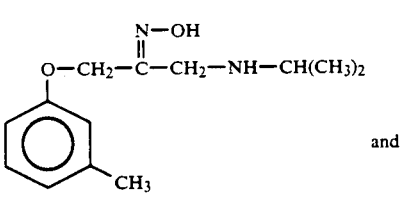

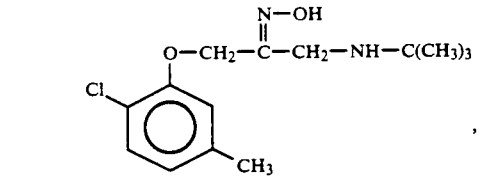

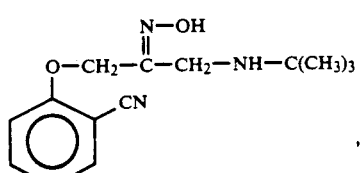

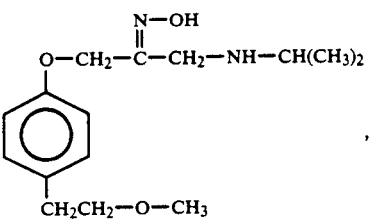

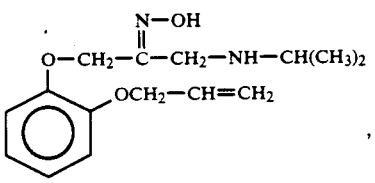

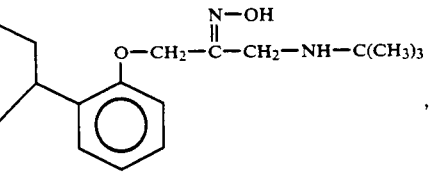

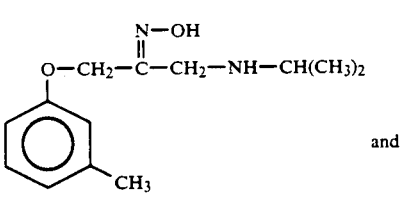

and

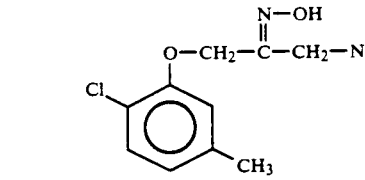

and the pharmaceutically acceptable acid addition salts thereof.

35. An ophthalmic composition of matter, in unit dosage form, for use in the treatment of glaucoma or in the lowering of intraocular pressure in a warm-blooded animal, said composition comprising an effective intraocular pressure reducing amount of a compound having the formula $$Ar-X-CH_2-\overset{\overset{Y}{\|}}{C}-CH_2-NHR \quad (I)$$

or a pharmaceutically acceptable acid addition salt thereof, wherein —X— is —O—, —CH$_2$— or —; =Y is a derivatized keto group which is hydrolyzable or enzymatically convertible to a keto group; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties; and a non-toxic ophthalmically acceptable carrier therefor.

36. A composition according to claim 35, wherein =Y is =NOH.

37. A composition according to claim 35, wherein —X— is —O—.

38. A composition according to claim 36, wherein —X— is —O—.

39. A composition according to claim 35, wherein Ar is selected from the group consisting of

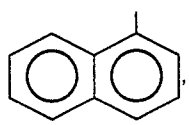 , 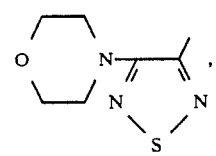 ,

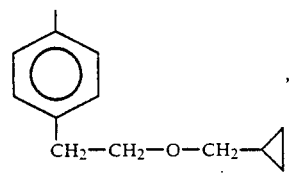 , 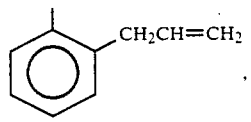 ,

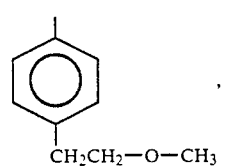 , 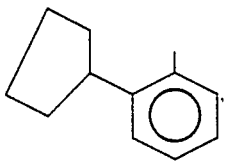 ,

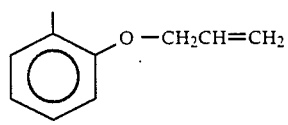 and 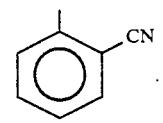 .

40. A composition according to claim 35, comprising an effective intraocular pressure reducing amount of a compound having the formula

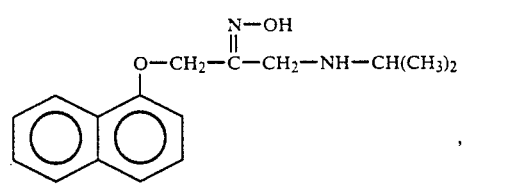 ,

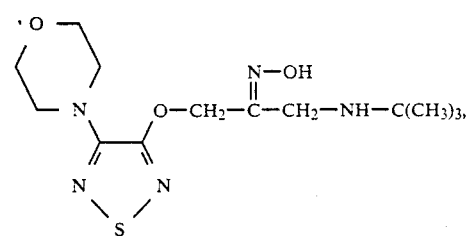 ,

-continued

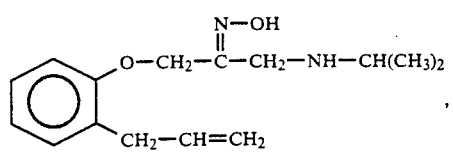 ,

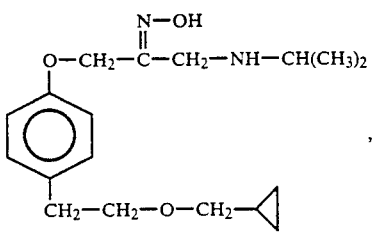 ,

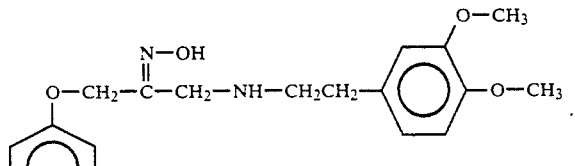 ,

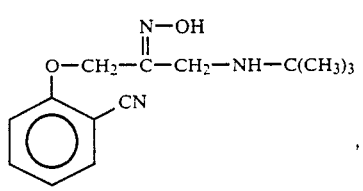 ,

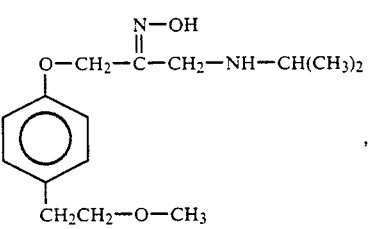 ,

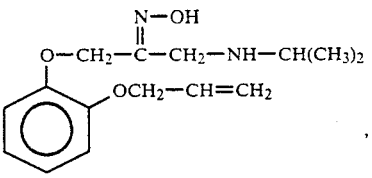 ,

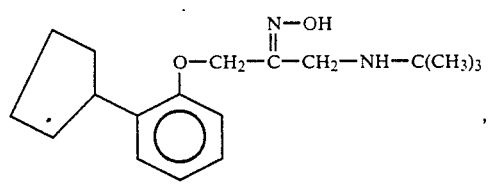 ,

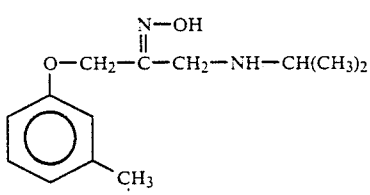 or

-continued

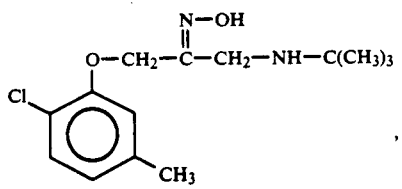

,

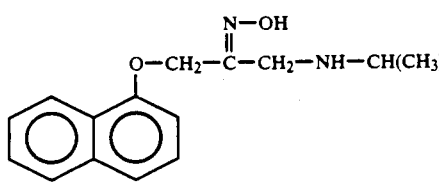

,

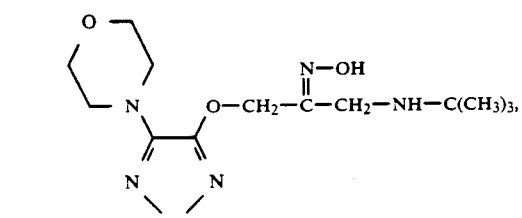

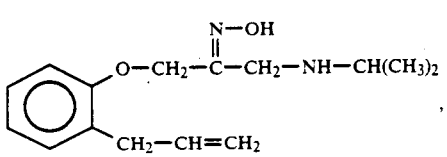

,

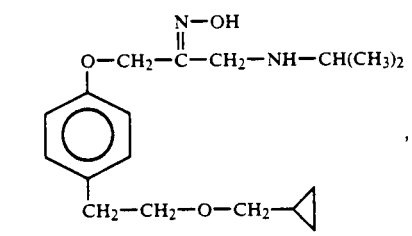

,

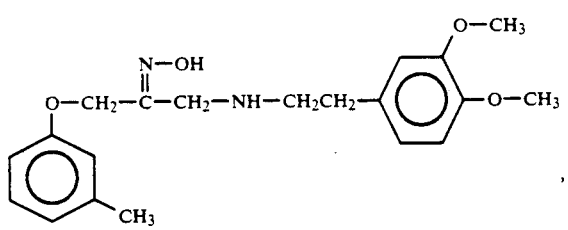

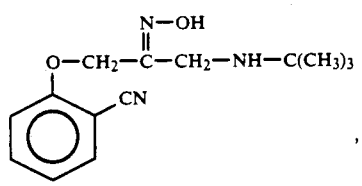

,

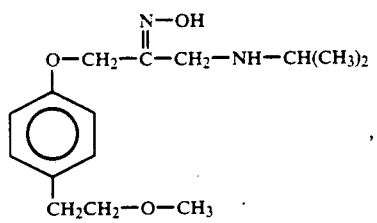

-continued

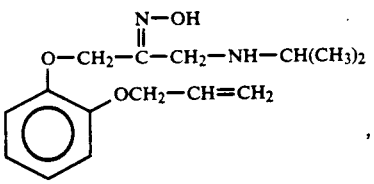

,

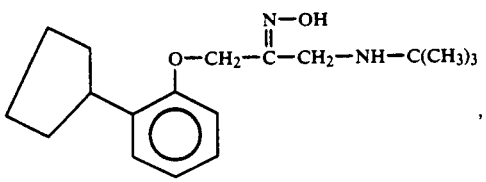

,

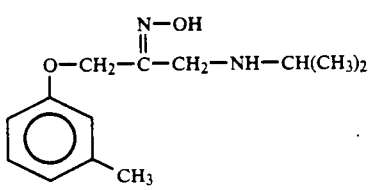

and

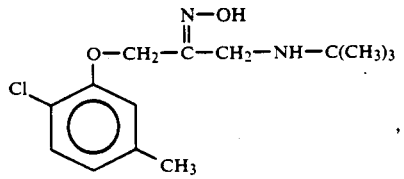

, or a pharmaceutically acceptable acid addition salt thereof.

41. A method for producing in the ocular tissue of a warm-blooded animal an effective intraocular pressure lowering amount of a β-adrenergic blocker of the formula $$Ar-X-CH_2-\underset{\underset{OH}{|}}{CH}-CH_2-NHR \qquad (II)$$

wherein —X— is —O—, —CH$_2$— or —; R is alkyl having from 1 to 12 carbon atoms or aralkyl having from 7 to 20 carbon atoms; and Ar is the 3-aromatic or heterocyclic residue of a 1-alkylamino-2-propanol having an aromatic or heterocyclic substituent at the 3-position and having β-adrenergic blocking properties; said method comprising administering to the eye or eyes of said animal a quantity of a precursor of said β-adrenergic blocker of formula (II) which is bioconvertible in ocular tissue into said β-adrenergic blocker of formula (II) via the corresponding ketone intermediate of the formula $$Ar-X-CH_2-\underset{\underset{O}{\|}}{C}-CH_2NHR \qquad (IV)$$

wherein Ar, X and R are defined as above, said quantity of said precursor being sufficient to result via the intermediate ketone in ultimate release of an effective intraocular pressure lowering amount of said β-adrenergic blocker of formula (II) in the ocular tissue of said animal.

42. A method according to claim 41, which results predominantly in stereospecific formation of the active intraocular pressure lowering enantiomer of the β-adrenergic blocker of formula (II).

43. A method according to claim 41, wherein the β-adrenergic blocker of formula (II) is selected from the group consisting of propranolol, timolol, carteolol, befunolol, metipranolol, betaxolol, bunolol, celiprolol, alprenolol, metoprolol, penbutolol, oxprenolol, bunitrolol, pindolol, atenolol, falintolol, ICI-118,551, moprolol, nadolol, bufuralol, IPS-339, labetolol, bevantolol, bupranolol, cetamolol, levobunolol, mepindolol and toliprolol.

44. A method according to claim 43, which results predominantly in stereospecific formation of the active intraocular pressure lowering enantiomer of the β-adrenergic blocker of formula (II).

45. A compound having the formula

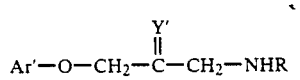

or a pharmaceutically acceptable acid addition salt thereof, wherein =Y' is =NOR$_1$, =N—NH$_2$ or =N—NR$_1$R$_2$ wherein R$_1$ and R$_2$ may be the same or different and are H or alkyl having from 1 to 8 carbon atoms; R is alkyl having from 1 to 12 carbon atoms or aralkyl having from 7 to 20 carbon atoms; and Ar' is the 3-aromatic residue of a 1-alkylamino-2-propanol having an aromatic substituent at the 3-position and having β-adrenergic blocking properties.

46. A compound or salt according to claim 45, wherein =Y is =NOR$_1$ wherein R$_1$ is H or alkyl having from 1 to 8 carbon atoms.

47. A compound or salt according to claim 46, wherein =Y is =NOH.

48. A compound or salt according to claim 46, wherein —X— is —O—.

49. A compound or salt according to claim 47, wherein —X— is —O—.

50. A compound or salt according to claim 45, wherein R is isopropyl, t-butyl, benzyl or 3,4-dimethoxyphenethyl.

51. A compound or salt according to claim 50, wherein R is isopropyl or t-butyl.

52. A compound or salt according to claim 51, wherein R is isopropyl.

53. A compound or salt according to claim 45, wherein Ar' is selected from the group consisting of

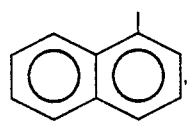 , 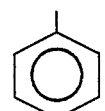 ,

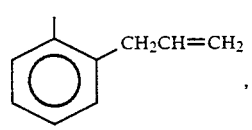 ,

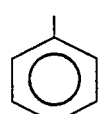

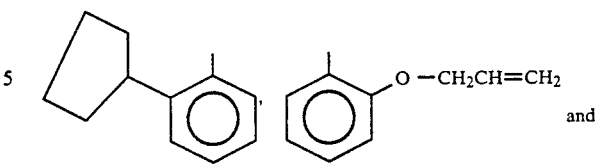 and

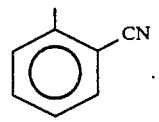.

54. A compound or salt according to claim 53, wherein Ar' is

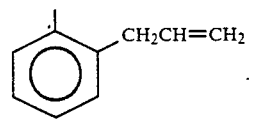

55. A compound according to claim 45, having the formula

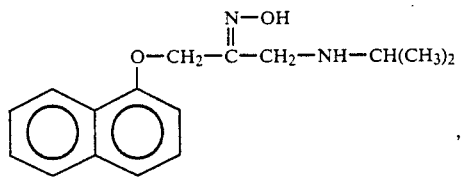 ,

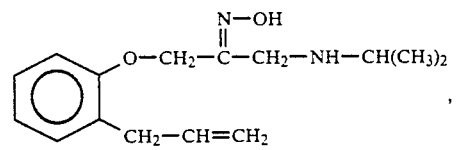 ,

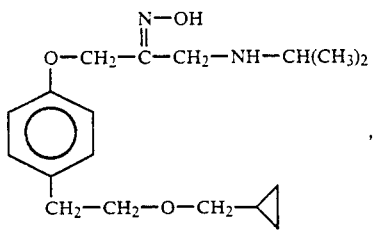 ,

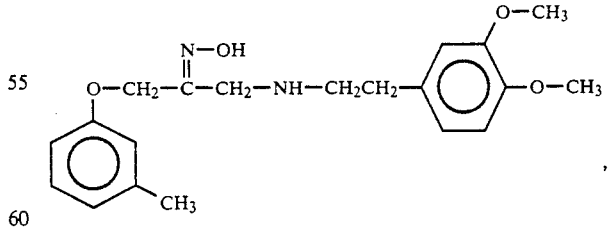 ,

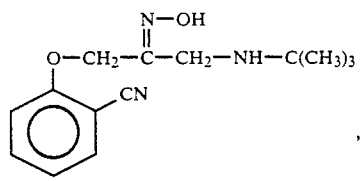 ,

-continued

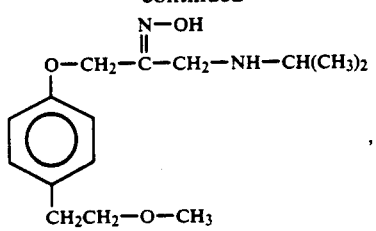

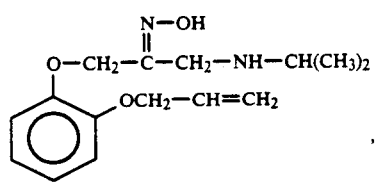

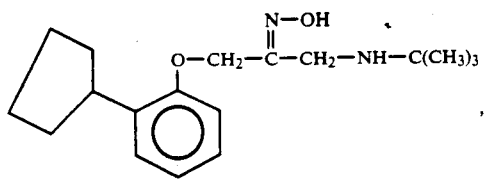

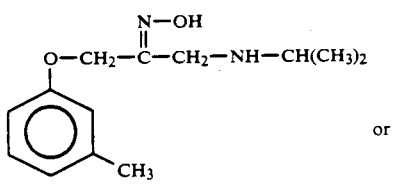

or

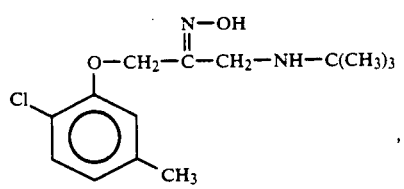

or a pharmaceutically acceptable acid addition salt thereof.

56. The compound of claim 45 having the formula

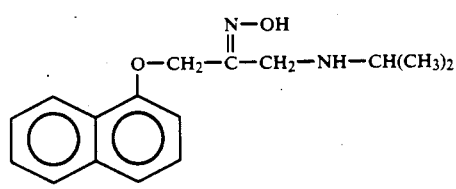

or a pharmaceutically acceptable acid addition salt thereof.

57. The compound of claim 45 having the formula

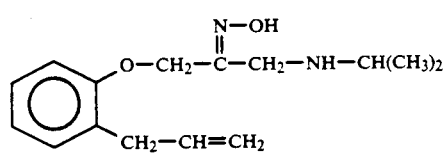

or a pharmaceutically acceptable acid addition salt thereof.

58. The compound of claim 45 having the formula

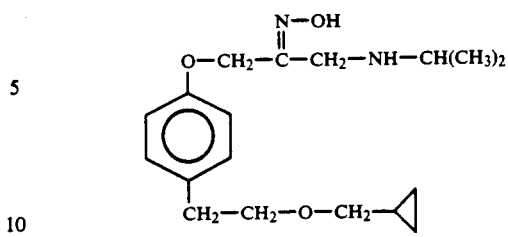

or a pharmaceutically acceptable acid addition salt thereof.

59. The compound of claim 45 having the formula

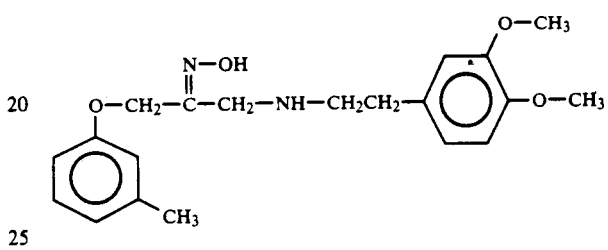

or a pharmaceutically acceptable acid addition salt thereof.

60. The compound of claim 45 having the formula

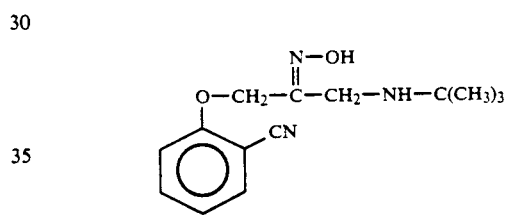

or a pharmaceutically acceptable acid addition salt thereof.

61. The compound of claim 45 having the formula

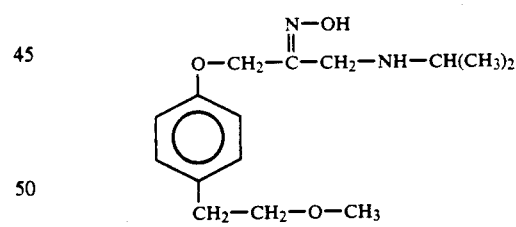

or a pharmaceutically acceptable acid addition salt thereof.

62. The compound of claim 45 having the formula

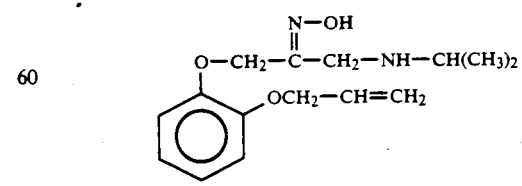

or a pharmaceutically acceptable acid addition salt thereof.

63. The compound of claim 45 having the formula

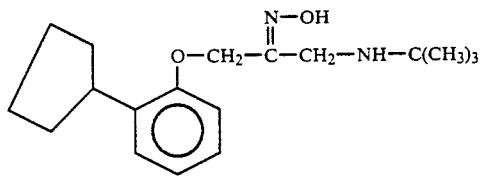

or a pharmaceutically acceptable acid addition salt thereof.

64. The compound of claim 45 having the formula

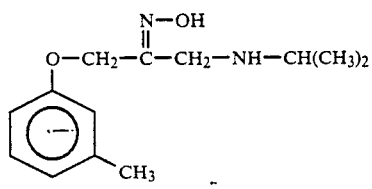

or a pharmaceutically acceptable acid addition salt thereof.

65. The compound of claim 45 having the formula

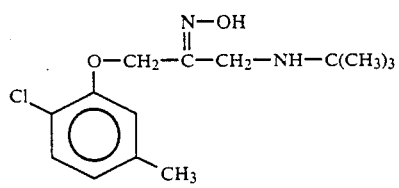

or a pharmaceutically acceptable acid addition salt thereof.

66. A method for eliciting a β-adrenergic blocking response in a warm-blooded animal in need thereof, which comprises administering to said animal an effective β-adrenergic blocking amount of a compound as claimed in claim 45 or a pharmaceutically acceptable acid addition salt thereof.

67. A method according to claim 66, wherein =Y' is =NOH.

68. A method according to claim 66, wherein Ar' is selected from the group consisting of

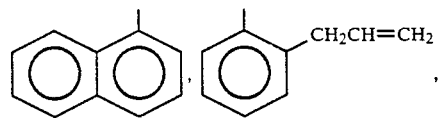

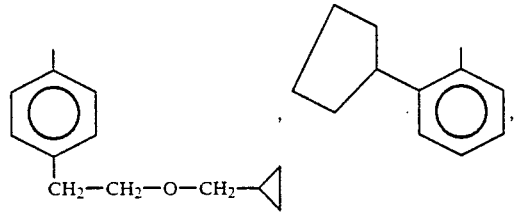

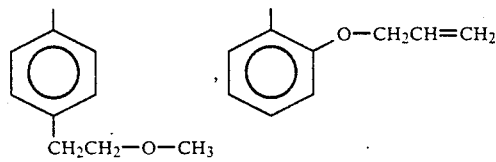

and 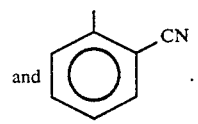

69. A method according to claim 66, wherein the compound administered is selected from the group consisting of

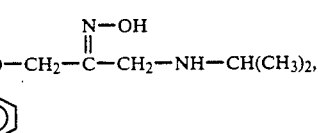

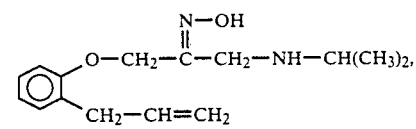

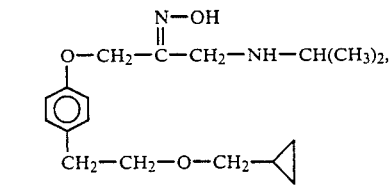

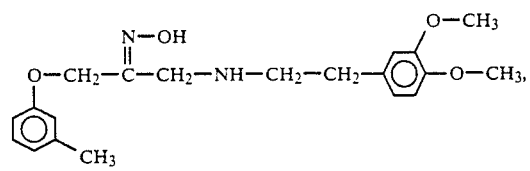

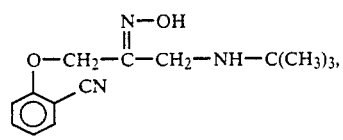

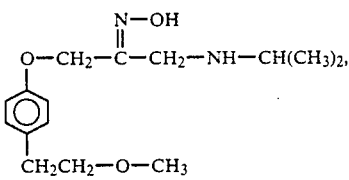

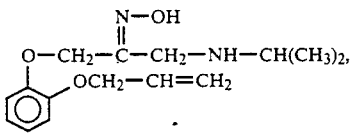

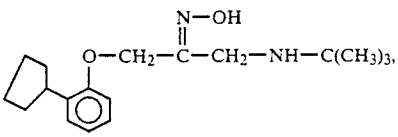

-continued

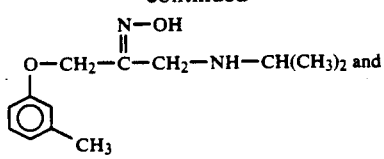 and

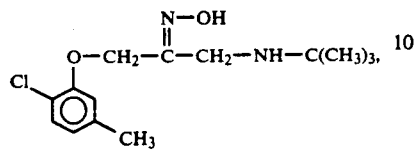

and the pharmaceutically acceptable acid addition salts thereof.

70. A pharmaceutical composition of matter, in unit dosage form, for use in eliciting a β-adrenergic blocking response in a warm-blooded animal, said composition comprising an effective β-adrenergic blocking amount of a compound as claimed in claim 47 or a pharmaceutically acceptable acid addition salt thereof, and a non-toxic pharmaceutically acceptable carrier therefor.

71. A composition according to claim 70, wherein =Y' is =NOH.

72. A composition according to claim 70, wherein Ar' is selected from the group consisting of

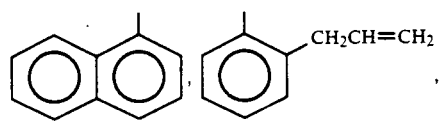

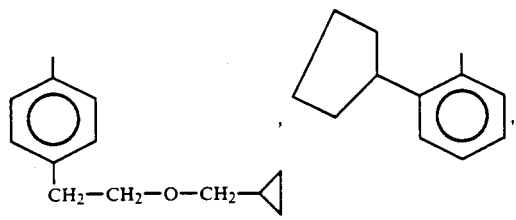

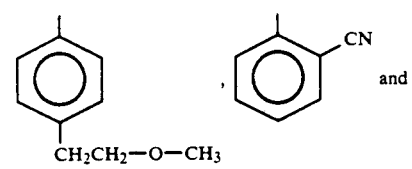 and

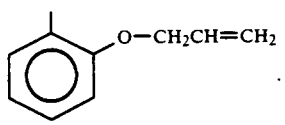

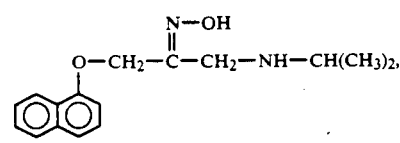

73. A composition according to claim 70, comprising an effective β-adrenergic blocking amount of a compound having the formula -continued

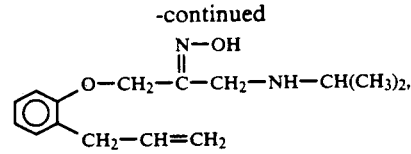

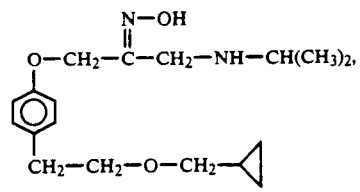

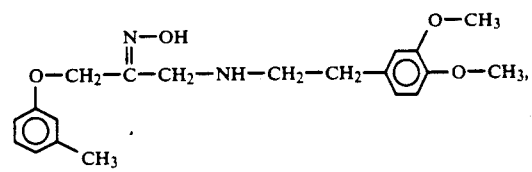

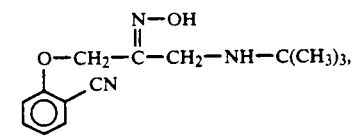

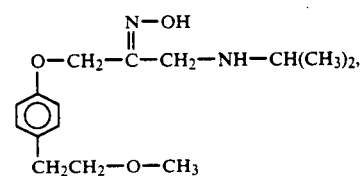

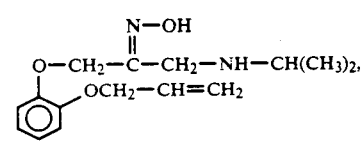

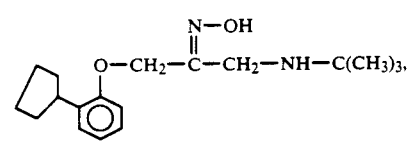

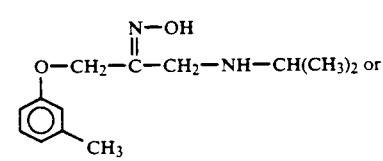

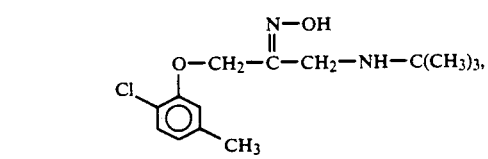

or a pharmaceutically acceptable acid addition salt thereof.

74. A method for the treatment of glaucoma or for lowering intraocular pressure in a warm-blooded animal in need thereof, which comprises administering to the eye or the eyes of said animal an effective intraocular pressure reducing amount of a compound as claimed in claim 47 or a pharmaceutically acceptable acid addition salt thereof.

75. A method according to claim 74, wherein =Y' is =NOH.

76. A method according to claim 74, wherein Ar' is selected from the group consisting of

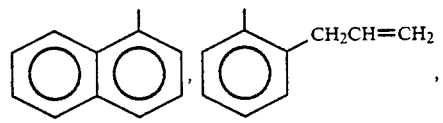,

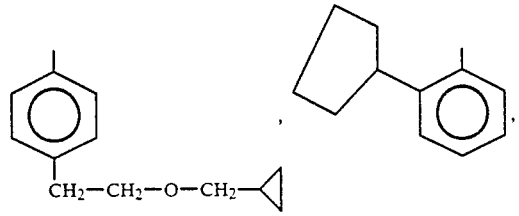,

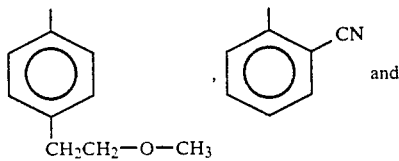, and

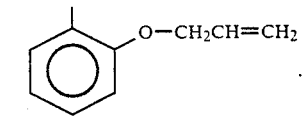

77. A method according to claim 74, wherein the compound administered is selected from the group consisting of

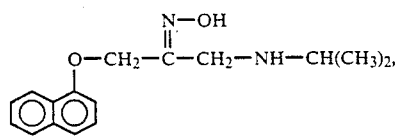,

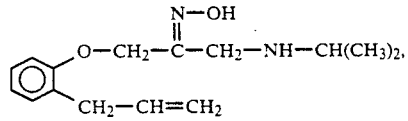,

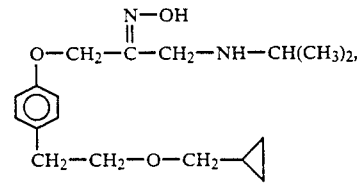,

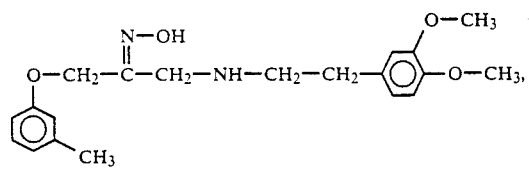,

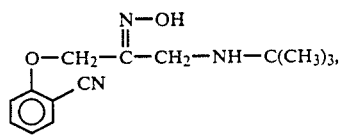,

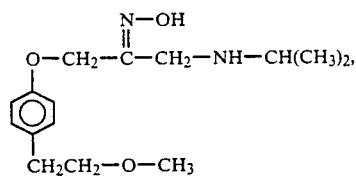,

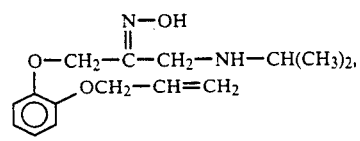,

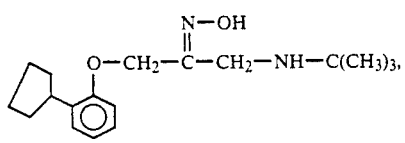,

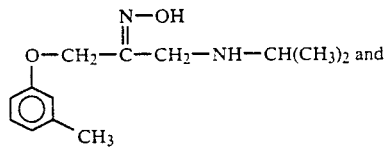 and

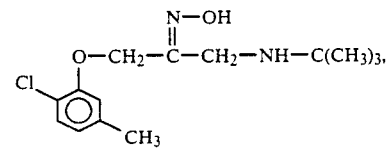, and the pharmaceutically acceptable acid addition salts thereof.

78. An ophthalmic composition of matter, in unit dosage form, for use in the treatment of glaucoma or in the lowering of intraocular pressure in a warm-blooded animal, said composition comprising an effective intraocular pressure reducing amount of a compound as claimed in claim 47 or a pharmaceutically acceptable acid addition salt thereof, and a non-toxic ophthalmically acceptable carrier thereof.

79. A composition according to claim 78, wherein =Y' is =NOH.

80. A composition according to claim 78, wherein Ar' is selected from the group consisting of

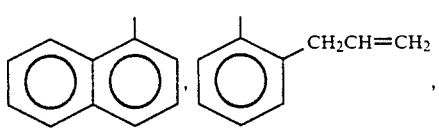

-continued

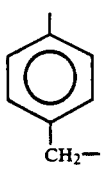 , 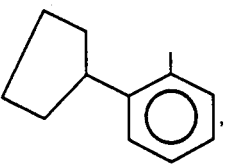

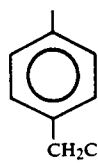 , 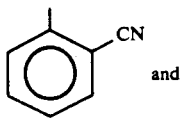 and

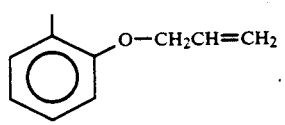

81. A composition according to claim 78, comprising an effective intraocular pressure reducing amount of a compound having the formula

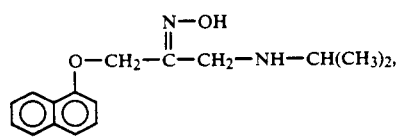

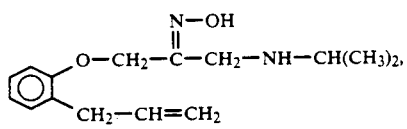

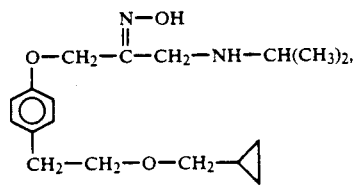

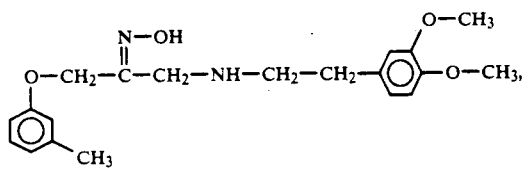

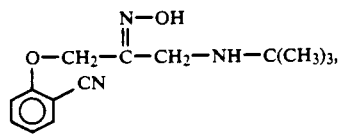

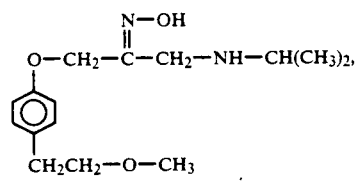

-continued

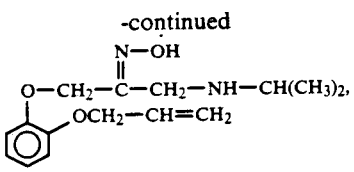

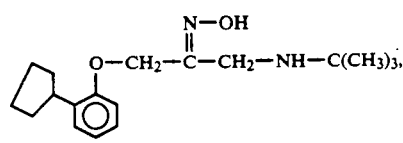

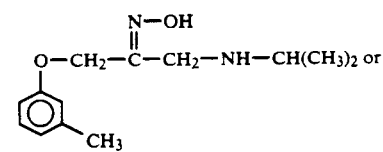

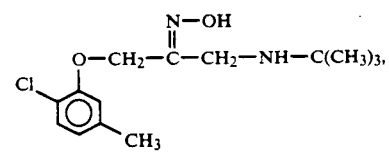

or a pharmaceutically acceptable acid addition salt thereof.

82. A method for producing in the ocular tissue of a warm-blooded animal an effective intraocular pressure lowering amount of a β-adrenergic blocker of the formula $$AR'—O—CH_2—\overset{OH}{\underset{|}{CH}}—CH_2—NHR \quad (II')$$

wherein R is alkyl having from 1 to 12 carbon atoms or aralkyl having from 7 to 20 carbon atoms and Ar' is the 3-aromatic residue of a 1-alkylamino-2-propanol having an aromatic substituent at the 3-position and having β-adrenergic blocking properties, said method comprising administering to the eye or eyes of said animal a quantity of a precursor of said β-adrenergic blocker of formula (II') which is bioconvertible in ocular tissue into said β-adrenergic blocker of formula (II') via the corresponding ketone intermediate of the formula $$AR'—O—CH_2—\overset{O}{\underset{||}{C}}—CH_2NHR \quad (IV')$$

wherein Ar' and R are defined as above, said quantity of said precursor being sufficient to result via the intermediate ketone in ultimate release of an effective intraocular pressure lowering amount of said β-adrenergic blocker of formula (II') in the ocular tissue of said animal.

83. A method according to claim 82, wherein said precursor is a compound having the formula $$Ar'—O—CH_2—\overset{Y'}{\underset{||}{C}}—CH_2NHR$$

or a pharmaceutically acceptable acid addition salt thereof, wherein Ar' and R are defined as above and =Y' is =NOR₁, =N-NH₂ or =N-NR₁R₂ wherein R₁ and $R_2$ may be the same or different and are H or alkyl having from 1 to 8 carbon atoms.

84. A method according to claim 82, which results predominantly in stereospecific formation of the active intraocular pressure lowering enantiomer of the β-adrenergic blocker of formula (II').

85. A method according to claim 82, wherein the β-adrenergic blocker of formula (II') is selected from the group consisting of propranolol, metipranolol, betaxolol, bunolol, celiprolol, alprenolol, metoprolol, penbutolol, oxprenolol, bunitrolol, atenolol, moprolol, nadolol, labetolol, bevantolol, bupranolol, cetamolol, levobunolol and toliprolol.

86. A method according to claim 85, which results predominantly in stereospecific formation of the active intraocular pressure lowering enantiomer of the β-adrenegeric blocker of formual (II').

* * * * *